(12) United States Patent  
Kasdan et al.

(10) Patent No.: US 8,945,913 B2
(45) Date of Patent: Feb. 3, 2015

(54) KITS, COMPOSITIONS AND METHODS FOR DETECTING A BIOLOGICAL CONDITION

(71) Applicant: Leukodx Ltd., Jerusalem (IL)

(72) Inventors: Harvey Lee Kasdan, Jerusalem (IL); Julien Meissonnier, Jerusalem (IL); Yoav Zuta, Jerusalem (IL); Bruce Davis, Jerusalem (IL); Micha Rosen, Jerusalem (IL); Yael Himmel, Jerusalem (IL); Yehoshua Broder, Jerusalem (IL)

(73) Assignee: LeukoDx Ltd., Jerusalem (IL)

( * ) Notice: Subject to any disclaimer, the term of this patent is extended or adjusted under 35 U.S.C. 154(b) by 0 days.

(21) Appl. No.: 14/296,317

(22) Filed: Jun. 4, 2014

(65) Prior Publication Data

US 2014/0287435 A1  Sep. 25, 2014

Related U.S. Application Data

(62) Division of application No. 13/716,246, filed on Dec. 17, 2012, now abandoned.

(51) Int. Cl.
*C12M 1/34*    (2006.01)
*C12M 3/00*    (2006.01)
(Continued)

(52) U.S. Cl.
CPC .............. *G01N 33/569* (2013.01); *B01L 3/502* (2013.01); *B01L 2400/0481* (2013.01)
USPC ....... 435/287.2; 435/7.1; 435/7.2; 435/283.1; 435/288.7; 435/288.5; 436/518; 436/524; 436/536; 436/164; 436/172

(58) Field of Classification Search
USPC ........... 436/518, 524, 536, 164, 172; 435/7.1, 435/7.2, 283.1, 288.7, 288.5, 287.2
See application file for complete search history.

(56) References Cited

U.S. PATENT DOCUMENTS

| 4,233,029 A | 11/1980 | Columbus |
| 4,376,820 A | 3/1983 | Giannini et al. |
| 4,400,370 A | 8/1983 | Kass |

(Continued)

FOREIGN PATENT DOCUMENTS

| WO | WO 2001/068238 A2 | 9/2001 |
| WO | WO 2006/055816 | 5/2006 |

(Continued)

OTHER PUBLICATIONS

Groselj-Grenc et al., Neutrophil and Monocyte CD64 and CD163 Expression in Critically Ill Neonates and Children with Sepsis: Comparison of Fluorescence Intensities and Calculated Indexes. 2008, Mediators of Inflammation, pp. 1-10.*

(Continued)

*Primary Examiner* — Melanie Y Brown
(74) *Attorney, Agent, or Firm* — Wilson Sonsini Goodrich & Rosati

(57) ABSTRACT

The present invention provides kits, apparatus and methods for determining a biological condition in a mammalian subject, the method includes incubating a specimen from a patient with at least one composition in a kit for a predetermined period of time to form at least one reaction product, when the subject has said biological condition, and receiving an indication of the at least one reaction product responsive to at least one reporter element in the kit thereby providing the indication of the biological condition in the subject.

16 Claims, 11 Drawing Sheets

(51) Int. Cl.
*G01N 33/569* (2006.01)
*B01L 3/00* (2006.01)

(56) References Cited

U.S. PATENT DOCUMENTS

| | | | |
|---|---|---|---|
| 4,882,284 | A | 11/1989 | Kirchanski et al. |
| 5,304,487 | A | 4/1994 | Wilding et al. |
| 5,716,852 | A | 2/1998 | Yager et al. |
| 5,837,115 | A | 11/1998 | Austin et al. |
| 5,972,710 | A | 10/1999 | Weigl et al. |
| 6,136,610 | A | 10/2000 | Polito et al. |
| 6,372,516 | B1 | 4/2002 | Sun |
| 6,426,230 | B1 * | 7/2002 | Feistel .................. 436/165 |
| 6,551,841 | B1 | 4/2003 | Wilding et al. |
| 6,635,163 | B1 | 10/2003 | Han et al. |
| 6,637,463 | B1 | 10/2003 | Lei et al. |
| 6,674,525 | B2 | 1/2004 | Bardell et al. |
| 6,852,284 | B1 | 2/2005 | Holl et al. |
| 7,105,355 | B2 | 9/2006 | Kurabayashi et al. |
| 7,192,560 | B2 | 3/2007 | Parthasarathy et al. |
| 7,247,274 | B1 | 7/2007 | Chow |
| 7,347,976 | B2 | 3/2008 | Parthasarathy et al. |
| 7,553,453 | B2 | 6/2009 | Gu et al. |
| 7,718,421 | B2 * | 5/2010 | Chen et al. .............. 435/288.5 |
| 669,191 | A1 | 10/2012 | Handique |
| 8,318,109 | B2 * | 11/2012 | Saltsman et al. .......... 422/502 |
| 8,364,418 | B2 | 1/2013 | Davis et al. |
| 8,518,705 | B2 | 8/2013 | Chan et al. |
| 2001/0008760 | A1 | 7/2001 | King et al. |
| 2002/0031255 | A1 | 3/2002 | Kasdan et al. |
| 2003/0002037 | A1 | 1/2003 | Kasdan et al. |
| 2003/0073089 | A1 | 4/2003 | Mauze et al. |
| 2003/0170881 | A1 | 9/2003 | Davis et al. |
| 2004/0126008 | A1 | 7/2004 | Chapoulaud et al. |
| 2005/0105077 | A1 | 5/2005 | Padmanabhan et al. |
| 2006/0011862 | A1 | 1/2006 | Bernstein |
| 2007/0227890 | A1 | 10/2007 | Ramsey et al. |
| 2007/0253868 | A1 | 11/2007 | Beebe et al. |
| 2007/0292941 | A1 | 12/2007 | Handique et al. |
| 2008/0101993 | A1 | 5/2008 | Andersson et al. |
| 2008/0212102 | A1 | 9/2008 | Nuzzo et al. |
| 2009/0042241 | A1 | 2/2009 | Yu-Chong et al. |
| 2009/0117605 | A1 * | 5/2009 | Davis et al. .................. 435/29 |
| 2010/0051124 | A1 | 3/2010 | Imran |
| 2010/0093019 | A1 * | 4/2010 | Ditcham et al. .............. 435/34 |
| 2011/0184537 | A1 | 7/2011 | Kasdan et al. |
| 2012/0071342 | A1 | 3/2012 | Lochhead et al. |
| 2012/0266986 | A1 | 10/2012 | Wimberger-Friedl et al. |
| 2012/0275972 | A1 | 11/2012 | Schoen et al. |
| 2013/0137135 | A1 | 5/2013 | Tai et al. |
| 2013/0230867 | A1 | 9/2013 | Davis et al. |

FOREIGN PATENT DOCUMENTS

| | | | |
|---|---|---|---|
| WO | WO 2006/118586 | A2 | 11/2006 |
| WO | WO 2008/121828 | | 10/2008 |
| WO | WO 2008/124589 | A2 | 10/2008 |
| WO | WO 2009/144660 | | 12/2009 |
| WO | WO 2011/094577 | A2 | 8/2011 |
| WO | WO 2011/128893 | A3 | 10/2011 |
| WO | WO 2012/092010 | | 7/2012 |
| WO | WO 2014/097286 | | 6/2014 |
| WO | WO 2014/097287 | | 6/2014 |

OTHER PUBLICATIONS

Adams, et al. Fluorometric characterization of six classes of human leukocytes. Acta Cytol. Sep.-Oct. 1974; 18(5): 389-391.

Adams, et al. Machine characterization of human leukocytes by acridine orange fluorescence. Acta Cytol. May-Jun. 1971; 15(3): 289-291.

Altendorf, et al. Differential Blood Cell Counts Obtained Using a Microchannel Based Flow Cytometer. Transducers. Jun. 16-19, 1997; 1: 531-534.

Assicot, et al. High serum procalcitonin concentrations in patients with sepsis and infection. Lancet. Feb. 27, 1993; 341(8844): 515-518.

Aulesa, et al. Validation of the Coulter LH 750 in a hospital reference laboratory. Lab Hematol. 2003; 9(1): 15-28.

Ault, Kenneth A. Flow cytometric measurement of platelet function and reticulated platelets. Annals of the New York Academy of Sciences. Mar. 20, 1993; 677: 293-308.

Bhattacharya, et al. Studies on Surface Wettability of Poly(Dimethyl) Siloxane (PDMS) and Glass Under Oxygen-Plasma Treatment and Correlation With Bond Strength. J. Microelectromechan. Syst. Jun. 2005; 14: 590-597.

Blajchman, et al. Bacterial detection of platelets: current problems and possible resolutions. Transfusion medicine reviews. Oct. 2005;19(4):259-272.

Bodensteiner, David C. A flow cytometric technique to accurately measure post-filtration white blood cell counts. Transfusion. Sep. 1989; 29(7): 651-653.

Cheson, et al. National Cancer Institute-sponsored Working Group guidelines for chronic lymphocytic leukemia: revised guidelines for diagnosis and treatment. Blood. 1996; 87(12): 4990-4997.

Christ-Crain, et al. Effect of procalcitonin-guided treatment on antibiotic use and outcome in lower respiratory tract infections: cluster-randomised, single-blinded intervention trial. Lancet. Feb. 21, 2004; 363(9409): 600-607.

Cristofanilli, et al. Circulating tumor cells, disease progression, and survival in metastatic breast cancer. N Engl J Med. Aug. 19, 2004; 351(8): 781-791.

Davis, et al. Neutrophil CD64 is an improved indicator of infection or sepsis in emergency department patients. Arch Pathol Lab Med. May 2006; 130(5): 654-661.

Dieye, et al. Absolute CD4 T-cell counting in resource-poor settings: direct volumetric measurements versus bead-based clinical flow cytometry instruments. J Acquir Immune Defic Syndr. May 1, 2005; 39(1): 32-37.

Divers, et al. Quantitation of CD62, soluble CD62, and lysosome-associated membrane proteins 1 and 2 for evaluation of the quality of stored platelet concentrates. Transfusion. Apr. 1995; 35(4): 292-297.

Drexler, et al. Diagnostic value of immunological leukemia phenotyping. Acta Haematol. 1986; 76(1): 1-8.

Dziegiel, et al. Detecting fetomaternal hemorrhage by flow cytometry. Curr Opin Hematol. Nov. 2006; 13(6): 490-495.

Fischer, et al. Reducing costs in flow cytometric counting of residual white blood cells in blood products: utilization of a single platform bead free flow rate calibration method. Transfusion. Jul. 2011; 51(7): 1431-1438.

Fujimoto, Keiji. Principles of Measurement in Hematology Analyzers Manufactured by Sysmex Corporation. Sysmex Journal International. 1999; 9(1): 31-44.

Gawad, et al. Micromachined impedance spectroscopy flow cytometer for cell analysis and particle sizing. Lab Chip. Sep. 2001; 1(1): 76-82.

Graff, et al. Close relationship between the platelet activation marker CD62 and the granular release of platelet-derived growth factor. J Pharmacol Exp Ther. Mar. 2002; 300(3): 952-957.

Guerti, et al. Performance evaluation of the Pentra 60C+ automated hematology analyzer and comparison with the ADVIA 2120. Int J Lab Hematol. Apr. 2009; 31(2): 132-141.

Hawkins, Robert C. Laboratory turnaround time. The Clinical Biochemist Reviews. Nov. 2007; 28(4): 179-194.

Hershman, et al. Monocyte HLA-DR antigen expression characterizes clinical outcome in the trauma patient. Br. J. Surg. Feb. 1990; 77(2): 204-207.

Hilfrich, et al. Prognostic relevance of human papillomavirus L1 capsid protein detection within mild and moderate dysplastic lesions of the cervix uteri in combination with p16 biomarker. Anal Quant Cytol Histol. Apr. 2008; 30(2): 78-82.

Hillier, et al. A case-control study of chorioamnionic infection and histologic chorioamnionitis in prematurity. N. Engl. J. Med. Oct. 13, 1988; 319(15): 972-978.

Hoffmann, Johannes JML. Neutrophil CD64 as a sepsis biomarker. Biochem Med (Zagreb). 2011; 21(3): 282-290.

(56) References Cited

OTHER PUBLICATIONS

Holmes, et al. High throughput particle analysis: combining dielectrophoretic particle focussing with confocal optical detection. Biosens Bioelectron. Feb. 15, 2006; 21(8): 1621-1630.
Hughes-Jones, et al. Differential white cell counts by frequency distribution analysis of cell volumes. J. Clin. Pathol. Aug. 1974; 27(8): 623-625.
IPRP and WO in PCT/US2008/059408, dated Oct. 6, 2009.
Jackson, JF. Supravital blood studies, using acridine orange fluorescence. Blood. May 1961; 17: 643-649.
Kass, L. Identification of lymphocyte subpopulations with a polymethine dye. J. Histochem. Cytochem. Jul. 1988; 36(7): 711-715.
Kass, L. Staining of granulocytic cells by Chlorazol black E. Am J. Clin. Pathol. Dec. 1981; 76(6): 810-812.
Kibe, et al. Diagnostic and prognostic biomarkers of sepsis in critical care. J Antimicrob Chemother. Apr. 2011; 66 Suppl 2: ii33-40.
Larosa, et al. Biomarkers: the future. Crit. Care Clin. Apr. 2011; 27(2): 407-419.
Lee, et al. A flow-rate independent counter using a fixed control volume between double electrical sensing zones. Proceedings of the 18th IEEE International Conference on Micro Electro Mechanical Systems (MEMS). 2005. 678-681.
Lee, et al. Micromachine-based multi-channel flow cytometers for cell/particle counting and sorting. J. Micromechanics and Microengineering. 2005; 15(3): 447-454.
Liu, et al. Improved quantitative Apt test for detecting fetal hemoglobin in bloody stools of newborns. Clin. Chem. Nov. 1993; 39(11 Pt 1): 2326-2329.
Lotan, et al. Bladder cancer screening in a high risk asymptomatic population using a point of care urine based protein tumor marker. J Urol. Jul. 2009; 182(1): 52-57.
Masse, et al. Validation of a simple method to count very low white cell concentrations in filtered red cells or platelets. Transfusion. Jul.-Aug. 1992; 32(6): 565-571.
Matic, et al. Whole blood analysis of reticulated platelets: improvements of detection and assay stability. Cytometry. Oct. 15, 1998; 34(5): 229-234.
McDonald, et al. Use of a solid-phase fluorescent cytometric technique for the detection of bacteria in platelet concentrates. Transfus Med. Jun. 2005; 15(3): 175-183.
Michelson, Alan D. Flow cytometry: a clinical test of platelet function. Blood. Jun. 15, 1996; 87(12): 4925-4936.
Miller, et al. Proteomics in Microfluidic Devices. In Encyclopedia of Micro- and Nanofluidics; Li, D. Q., Ed.; Springer: Heidelberg, Germany, 2008; 3: 1749-1758.
Morgan, et al. High speed simultaneous single particle impedance and fluorescence analysis on a chip. Curr. Appl. Phys. 2006; 6: 367-370.
Moriyama, et al. Acridine Orange as a Fluorescent Probe for Lysosomal Proton Pump3. J. Biochem. 1982; 92: 1333-1336.
Moro, et al. A new broad-spectrum cancer marker. Vitro Diagnostic Technology. Jun. 2005 1; 1-3.
Niehren, et al. An All-Solid-State Flow Cytometer for Counting Fluorescent Microspheres. Anal. Chem. 1995; 67(15): 2666-2671.
OA in CN 200880015296.7, dated Oct. 18, 2011.
OA in CN 200880015296.7, dated Sep. 20, 2012.
Oberjat, et al. Rapid and reliable differential counts on dilute leukocyte suspensions. J. Lab. Clin. Med. Sep. 1970; 76(3): 518-522.
Perry, et al. Is low monocyte HLA-DR expression helpful to predict outcome in severe sepsis? Intensive Care Med. Aug. 2003;29(8):1245-1252.
Ramakumar, et al. Comparison of screening methods in the detection of bladder cancer. J Urol. Feb. 1999; 161(2): 388-394.
Rawstron, et al. Quantitation of minimal disease levels in chronic lymphocytic leukemia using a sensitive flow cytometric assay improves the prediction of outcome and can be used to optimize therapy. Blood. Jul. 1, 2001; 98(1): 29-35.
Rodriguez, et al. A microchip CD4 counting method for HIV monitoring in resource-poor settings. PLoS Med. Jul. 2005; 2(7): e182.
Rylatt, et al. An immunoassay for human D dimer using monoclonal antibodies. Thromb Res. Sep. 15, 1983; 31(6): 767-778.
Sacks, et al. Guidelines and recommendations for laboratory analysis in the diagnosis and management of diabetes mellitus. Clin Chem. Mar. 2002; 48(3): 436-472.
Satake, et al. A sensor for blood cell counter using MEMS technology. Sensors and Actuators B: Chemical. 2002; 83(1): 77-81.
Segal, et al. Accuracy of platelet counting haematology analysers in severe thrombocytopenia and potential impact on platelet transfusion. Br. J. Haematol. Feb. 2005; 128(4): 520-525.
Shapiro, et al. Combined blood cell counting and classification with fluorochrome stains and flow instrumentation. J Histochem Cytochem. Jan. 1976; 24(1): 396-411.
Shapiro, et al. Cytomat-R: a computer-controlled multiple laser source multiparameter flow cytophotometer system. J Histochem Cytochem. Jul. 1977; 25(7): 836-844.
Sheehan, et al. An improved method of staining leucocyte granules with Sudan black B. J Pathol Bacteriol. Jan.-Apr. 1947; 59(1-2): 336-337.
Simonnet, et al. High-throughput and high-resolution flow cytometry in molded microfluidic devices. Anal Chem. Aug. 15, 2006; 78(16): 5653-5663.
Stein, et al. D-dimer for the exclusion of acute venous thrombosis and pulmonary embolism: a systematic review. Ann Intern Med. Apr. 20, 2004; 140(8): 589-602.
Steinkamp, et al. Multiparameter Cell Sorting: Identification of Human Leukocytes by Acridine Orange Fluorescence. Acta Cytol. 1973; 17: 113-117.
Sutherland, et al. The ISHAGE guidelines for CD34+ cell determination by flow cytometry. J Hematother. Jun. 1996; 5(3): 213-226.
Tatsumi, et al. Principle of blood cell counter—development of electric impedance method. Sysmex J. Int. 1999; 9(1): 8-20.
Tibbe, et al. Optical tracking and detection of immunomagnetically selected and aligned cells. Nat Biotechnol. Dec. 1999; 17(12): 1210-1213.
Van Dilla, et al. Volume distribution and separation of normal human leucocytes. Proc. Soc. Exp. Bio. Med. Jun. 1967; 125(2):367-370.
Wang, et al. "Reticulated platelets predict platelet count recovery following chemotherapy." Transfusion. Mar. 2002; 42(3): 368-374.
Weigl, et al. Design and rapid prototyping of thin-flim laminate-based microfluidic devices. Biomed Microdev. 2001; 3: 267-274.
Yang, et al. A cell counting/sorting system incorporated with a microfabricated flow cytometer chip. Meas. Sci. Technol. 2006; 17: 2001-2009.

\* cited by examiner

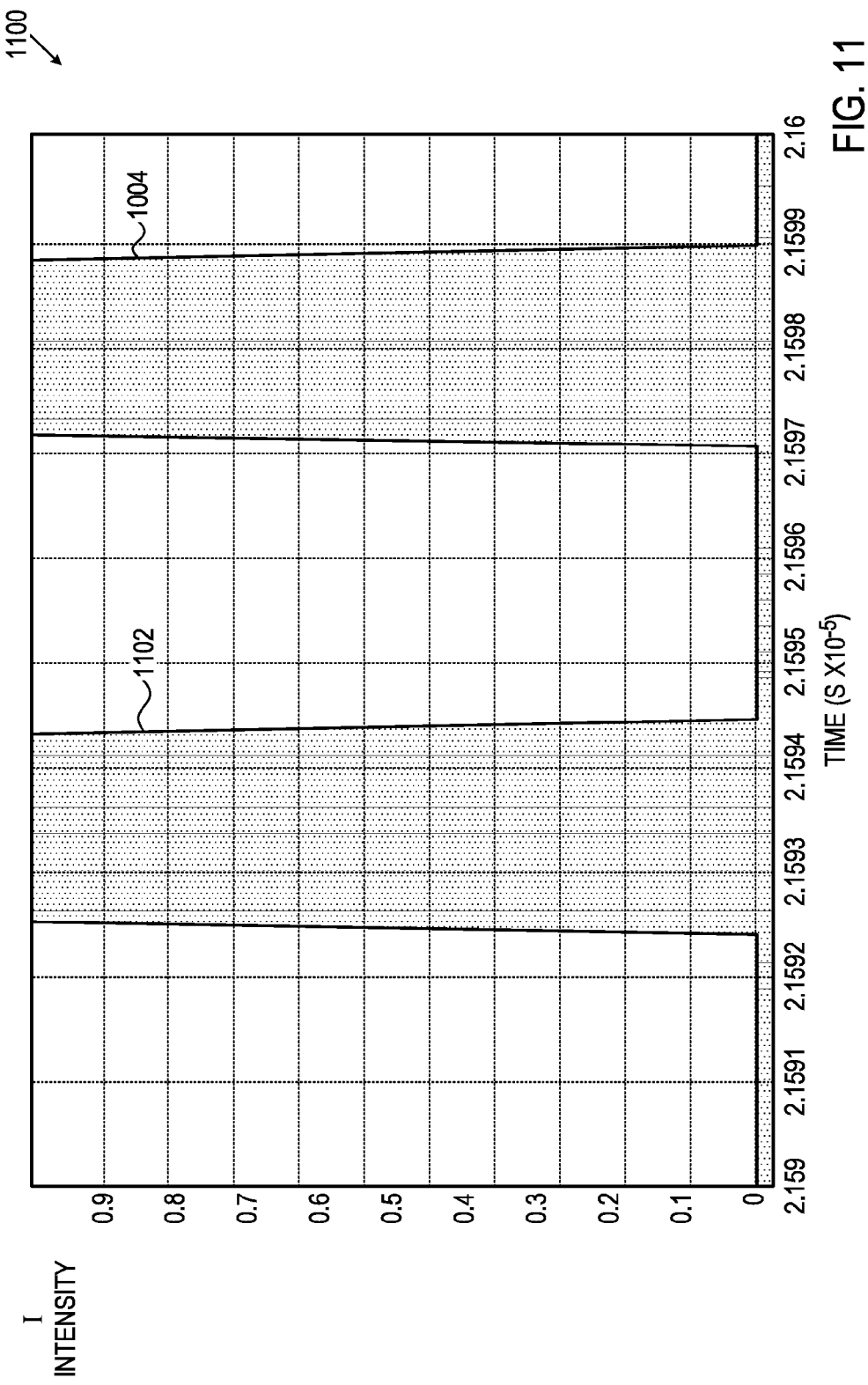

KITS, COMPOSITIONS AND METHODS FOR DETECTING A BIOLOGICAL CONDITION

CROSS-REFERENCE

This application is a divisional application of Ser. No. 13/716,246, filed Dec. 17, 2012, which is incorporated herein by reference in its entirety.

The disclosures of the co-pending U.S. Provisional Patent Application to Kasdan, et al, filed on Nov. 17, 2012, and titled "Kits, Compositions and Methods for Detecting a Biological Condition" and the co-pending U.S. Provisional Patent Application to Kasdan, et al, filed on Nov. 17, 2012, and titled "Kits, Compositions and Methods for Rapid Chemical Detection" are incorporated herein by reference in their entirety.

FIELD OF THE INVENTION

The present invention relates generally to apparatus and methods for detecting a biological condition, and more specifically to methods and apparatus for detecting a biological condition in small fluid samples.

BACKGROUND OF THE INVENTION

There are numerous medical conditions which are hard to diagnose. Often diagnosis by a physician is based on the physician's observation of combinations of symptoms in a patient. This sometimes leads to misdiagnosis. Furthermore, the patient's response to a treatment, whether drug or other modality is often followed up by physician's observation.

Many laboratory tests are performed in the diagnostic arena on a bodily specimen or fluid to determine a biological condition in a patient. However, these tests are performed off-line in diagnostic laboratories. Often, the laboratory services are only provided during a single 8-hour shift during the day and tend to be labor intensive. Some prior art publications in the field include, inter alia, U.S. Pat. No. 8,116,984, US2006215155 and US2012187117.

Despite the inventions mentioned hereinabove, there still remains an unmet need to provide improved apparatus and methods for detecting and diagnosing biological conditions in a patient.

SUMMARY OF THE INVENTION

It is an object of some aspects of the present invention to provide improved apparatus and methods for detecting and diagnosing biological conditions in a patient.

In some embodiments of the present invention, improved methods, apparatus and kits are provided for detecting and diagnosing a biological condition in a patient.

In other embodiments of the present invention, a method and kit is described for providing rapid detection of biological moieties in a sample from a patient.

In further embodiments of the present invention, a method and kit is disclosed for providing detection of biological moieties in a small fluid sample from a patient.

There is thus provided according to an embodiment of the present invention, a kit for evaluating a biological condition in a patient, the kit comprising;
a) a disposable element for receiving a biological specimen and for combining said specimen with at least one composition;
b) at least one composition comprising at least one detector moiety adapted to react with said specimen to form a reaction product, when said patient has said biological condition; and
c) at least one reporter element adapted to provide an indication of reaction product thereby providing the indication of the biological condition. Additionally, according to an embodiment of the present invention, the kit further comprises;
d) instructions for using the kit.

Furthermore, according to an embodiment of the present invention, the disposable element is a disposable cartridge.

Moreover, according to an embodiment of the present invention, the disposable cartridge is a disposable microfluidics cartridge.

Additionally, according to an embodiment of the present invention, the disposable microfluidics cartridge comprises at least one of the following elements:
a) a reservoir;
b) a pump;
c) a valve;
d) a conduit;
e) a motor;
f) a miniaturized flow cell;
g) a transport channel;
h) a microfluidic element;
i) a compressed gas holding element;
j) a compressed gas releasing element;
k) a nozzle element;
l) a mixing element;
m) a bellows element;
n) software adapted to activate said elements according to a specific sequence; and
o) hardware to activate said elements according to a specific sequence.

Additionally, according to an embodiment of the present invention, the disposable microfluidics cartridge comprises at least two of the elements.

Additionally, according to an embodiment of the present invention, the disposable microfluidics cartridge comprises at least three of the elements.

Additionally, according to an embodiment of the present invention, the disposable microfluidics cartridge comprises at least four of the elements.

Additionally, according to an embodiment of the present invention, the disposable microfluidics cartridge comprises at least five of the elements.

Additionally, according to an embodiment of the present invention, the disposable microfluidics cartridge comprises at least ten of the elements.

Additionally, according to an embodiment of the present invention, the disposable microfluidics cartridge comprises at least twenty of the elements.

Additionally, according to an embodiment of the present invention, the disposable microfluidics cartridge comprises at least thirty of the elements.

According to an embodiment of the present invention, the microfluidics kit is configured to provide the rapid indication with one hour.

According to another embodiment of the present invention, the microfluidics kit is configured to provide the rapid indication with thirty minutes.

According to another embodiment of the present invention, the microfluidics kit is configured to provide the rapid indication with fifteen minutes.

According to another embodiment of the present invention, the microfluidics kit is configured to provide the rapid indication with ten minutes.

According to another embodiment of the present invention, the microfluidics kit is configured to provide the rapid indication with five minutes.

According to another embodiment of the present invention, the microfluidics kit is configured to provide the rapid indication with one minute.

According to another embodiment of the present invention, the microfluidics kit is configured to provide the rapid indication with thirty seconds.

According to another embodiment of the present invention, the microfluidics kit is configured to provide the rapid indication with ten seconds.

According to another embodiment of the present invention, the microfluidics kit is configured to provide the rapid indication with one second.

There is thus provided according to an embodiment of the present invention, a microfluidics assay kit for performing a rapid biological assay, the kit comprising;
 a) a disposable element comprising a reactant, the disposable element being adapted to receive a sample comprising a biological entity and for combining said reactant with said biological entity to form a reaction product; and
 b) at least one reporter element adapted to provide a rapid indication of disappearance of said reactant thereby providing rapid assay of the biological entity.

There is thus provided according to an embodiment of the present invention, a microfluidics assay kit for performing a rapid assay of a biological entity, the kit comprising;
 a) a disposable element comprising a reactant, the disposable element being adapted to receive a sample comprising the biological entity and for combining said reactant with said biological entity to form a reaction product; and
 b) at least one reporter element adapted to provide a rapid indication of appearance of said reaction product thereby providing rapid assay of the biological entity.

There is thus provided according to an embodiment of the present invention, a composition for evaluating a biological condition, the composition comprising;
 a. a sample composition comprising at least one of;
  i. a bodily specimen comprising a target moiety;
  ii. a positive control moiety; and
  iii. a negative control moiety;
 b. a detection composition comprising at least one of;
  i. at least one target antibody;
  ii. at least one positive control identifying antibody; and
  iii. at least one negative control identifying detection moiety or characteristic; and
 c. at least one reference composition comprising at least one of;
  i. a target signal reference composition; and
  ii. a reference identifier composition.

There is thus provided according to another embodiment of the present invention a composition for evaluating a biological condition, the composition comprising;
 a. a sample composition comprising at least one of;
  i. a bodily specimen comprising a target moiety;
  ii. a positive control moiety; and
  iii. a negative control moiety;
 b. an antibody composition comprising at least one of;
  i. at least one target antibody (CD64 antibody);
  ii. at least one positive control identifying antibody (CD163); and
  iii. at least one negative control identifying antibody or characteristic; and
 c. at least one reference composition comprising at least one of;
  i. a target signal reference composition; and
  ii. a reference identifier composition.

Additionally, according to an embodiment of the present invention, the composition further comprises at least one conditioning moiety comprising;
 a. at least one lysis reagent; and
 b. at least one diluent.

Furthermore, according to an embodiment of the present invention, the biological condition is selected from a group consisting of blood diseases such as leukemia, thrombocytopenia immune system disorders, local infections, urinary tract disorders, autoimmune diseases and sepsis.

Moreover, according to an embodiment of the present invention the bodily specimen is selected from a group consisting of blood, serum, plasma, urine, saliva, cerebrospinal fluid (CSF), serous fluid, peritoneal fluid and synovial fluid.

According to another embodiment of the present invention, the target moiety includes a CD64 surface antigen on neutrophils.

Additionally, according to a further embodiment of the present invention, the positive control moiety includes monocytes and the negative control includes lymphocytes. Additionally, according to an embodiment of the present invention, the target moiety is CD64 on neutrophils, the positive control moiety includes CD64 expression on monocytes, and the negative control moiety includes lymphocytes without CD64 expression.

Further, according to an embodiment of the present invention, the target indicator is bound to a signaling moiety on the at least one target antibody.

Yet further, according to an embodiment of the present invention, the at least one reference composition includes beads.

Additionally, according to an embodiment of the present invention, the beads include polystyrene microbeads.

Moreover, according to an embodiment of the present invention, the target antibody reference composition includes a first fluorescent signal and the reference identifier composition includes a second fluorescent signal.

Furthermore, according to an embodiment of the present invention, the first fluorescent signal includes FITC and the second fluorescent signal includes Starfire Red fluor.

There is thus provided according to an embodiment of the present invention, a method of quantifying a biomarker in a sample, comprising;
 a. contacting the sample with a fluorescently-labeled binding moiety that specifically binds to the biomarker;
 b. detecting a first fluorescent signal from at least a portion of the labeled sample;
 c. detecting a second fluorescent signal from a population of fluorescently-labeled particles, wherein the population includes a known fluorescent intensity over a fixed time; and
 d. normalizing the first fluorescent signal to the second fluorescent signal, thereby quantifying the biomarker, wherein the normalizing includes using a device comprising software capable of comparing the first and second fluorescent signal.

Furthermore, according to an embodiment of the present invention, the biomarker is a sepsis biomarker.

Moreover, according to an embodiment of the present invention, the biomarker is CD64 or CD163.

Additionally, according to an embodiment of the present invention, the sample is a blood sample.

According to another embodiment of the present invention, the fluorescent label of the binding moiety and the fluorescent label of the particles is the same fluorescent label.

Further, according to an embodiment of the present invention, the binding moiety is an antibody.

According to an embodiment of the present invention, the software is capable of recognizing a specific lot of fluorescently-labeled particles.

Moreover, according to an embodiment of the present invention, the individual fluorescent signals include at least one first fluorescent signal and at least one second fluorescent signal.

Additionally, according to an embodiment of the present invention the fluorescently-labeled binding moiety targets a first cell population and a second cell population in the sample.

According to another embodiment of the present invention the detection of binding of the binding moiety to the second cell population provides an internal positive control for the sample.

Furthermore, according to an embodiment of the present invention, the binding moiety is anti-CD64 antibody and the first cell population includes polymorphonuclear leukocytes.

Yet further, according to an embodiment of the present invention, the second cell population includes monocytes.

According to an embodiment of the present invention, the method further comprises the step of determining the presence of at least one cell population in the sample that is not bound by the binding moiety, thus providing an internal negative control for the sample.

There is thus provided according to another embodiment of the present invention, a composition for evaluating a biological condition, the composition comprising;
 a. a sample comprising at least one of;
  i. a bodily specimen comprising a target moiety;
  ii. a positive control moiety; and
  iii. a negative control moiety;
 b. an antibody composition comprising at least one of;
  i. at least one target antibody;
  ii. at least one positive control identifying antibody; and
  iii. at least one negative control identifying antibody or characteristic; and
 c. at least one reference composition comprising at least one of;
  i. a target antibody reference composition; and
  ii. a reference identifier composition.

According to an embodiment of the present invention, the composition further comprises at least one conditioning moiety comprising;
 a) at least one lysis reagent; and
 b) at least one diluent.

There is thus provided according to another embodiment of the present invention, a method of determining the presence or absence of sepsis in a subject, the method including;
 a) contacting a blood sample from the subject with a fluorescently-labeled binding moiety specific to a sepsis marker, wherein the volume of the blood sample is 50 µL or smaller; and
 b) detecting the presence, absence or level of the binding moiety in the sample, thereby determining the presence or absence of sepsis in the subject.

There is thus provided according to another embodiment of the present invention, a method of quantifying a biomarker in a sample, comprising;
 a) contacting the sample with a fluorescently-labeled binding moiety that specifically binds to the biomarker;
 b) detecting a first fluorescent signal from at least a portion of the labeled sample;
 c) detecting a second fluorescent signal from a population of fluorescently-labeled particles, wherein the population includes a known fluorescent intensity over a fixed time; and
 d) normalizing the first fluorescent signal to the second fluorescent signal, thereby quantifying the biomarker, wherein the normalizing includes using a device comprising software capable of comparing the first and second fluorescent signal.

According to some embodiments, the sample may be liquid, according to other embodiments, the sample may be a colloid or suspension. According to further embodiments, the sample may be a solid, such as in a powder or crystal form.

Typical turnaround times for diagnostic prior art assays are 30-120 minutes. Often, the time lost in waiting for laboratory results can lead to a further deterioration in a patient, and sometimes death. In some cases, the physician has to act without having the laboratory results. This can lead to providing the patient with the wrong treatment. The present invention provides rapid assays to save lives and provide fast correct treatments to a patient.

There is thus provided according to an embodiment of the present invention automated method of determining the presence or absence of sepsis in a subject, including;
 a) contacting a blood sample from the subject with a fluorescently-labeled binding moiety specific to a sepsis marker, wherein the volume of the blood sample is 50 µL or smaller; and
 b) detecting the presence, absence or level of the binding moiety in the sample, thereby determining the presence or absence of sepsis in the subject within twenty minutes.

Additionally, according to an embodiment of the present invention, the sepsis marker is CD64.

Furthermore, according to an embodiment of the present invention, a second sepsis marker is CD163.

Moreover, according to an embodiment of the present invention, the method further includes contacting the blood sample with a second fluorescently-labeled binding moiety specific for a second sepsis marker.

Further, according to an embodiment of the present invention, the sepsis marker is CD64 and the second sepsis marker is CD163.

Additionally, according to an embodiment of the present invention, the binding moiety is an antibody.

Moreover, according to an embodiment of the present invention, the detecting step is performed in a device capable of receiving the sample and capable of detecting the binding moiety.

Additionally, according to an embodiment of the present invention, the method further includes the step of calibrating the device by detecting a population of the fluorescently-labeled particles.

According to another embodiment of the present invention, the particles include the same fluorescent label as the fluorescently-labeled binding moiety.

Additionally, according to an embodiment of the present invention, the method further includes a second population of particles that include the same fluorescent label as the second fluorescently-labeled binding moiety.

Moreover, according to an embodiment of the present invention, the method further includes performing an internal calibration after the detecting the fluorescently-labeled binding moiety.

Notably, according to an embodiment of the present invention, the calibration is completed in less than 5 minutes.

According to some embodiments, the particles are microbeads.

Additionally, according to an embodiment of the present invention, the method is performed in less than 15 minutes.

Furthermore, according to an embodiment of the present invention, the method, further includes the step of determining the presence of at least one cell population in the sample that is not bound by the binding moiety, thus providing an internal negative control for the sample.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration showing an apparatus for detecting a biological condition, in accordance with an embodiment of the present invention;

FIG. 2 is a simplified flow chart of a method for detecting a biological condition, in accordance with an embodiment of the present invention;

FIG. 3 is a simplified schematic illustration showing a methodology for detecting a biological condition associated with a CD64 cell surface antigen, in accordance with an embodiment of the present invention;

FIG. 4 is a simplified flow chart of a method for detecting a biological condition associated with a CD64 cell surface antigen, in accordance with an embodiment of the present invention;

FIG. 5A is a graphical output of a fluorescent detection assay of a non-activated neutrophil signature associated with the method of FIGS. 3-4, in accordance with an embodiment of the present invention;

FIG. 5B is a graphical output of a fluorescent detection assay of an activated neutrophil signature, associated with the method of FIGS. 3-4, in accordance with an embodiment of the present invention;

FIG. 5C is a graphical output of a fluorescent detection assay of a monocyte signature, associated with the method of FIGS. 3-4, in accordance with an embodiment of the present invention;

FIG. 5D is a graphical output of a fluorescent detection assay of a reference bead signature, associated with the method of FIGS. 3-4, in accordance with an embodiment of the present invention;

FIG. 6 is a simplified flow chart of a method for differentiating between different particles, in accordance with an embodiment of the present invention;

FIG. 7 is a graphical output of fluorescence from reference beads in eight wavebands, in accordance with an embodiment of the present invention;

FIG. 8 is a graphical output of data from FIG. 7 after a first mathematical manipulation, in accordance with an embodiment of the present invention;

Figure 7:
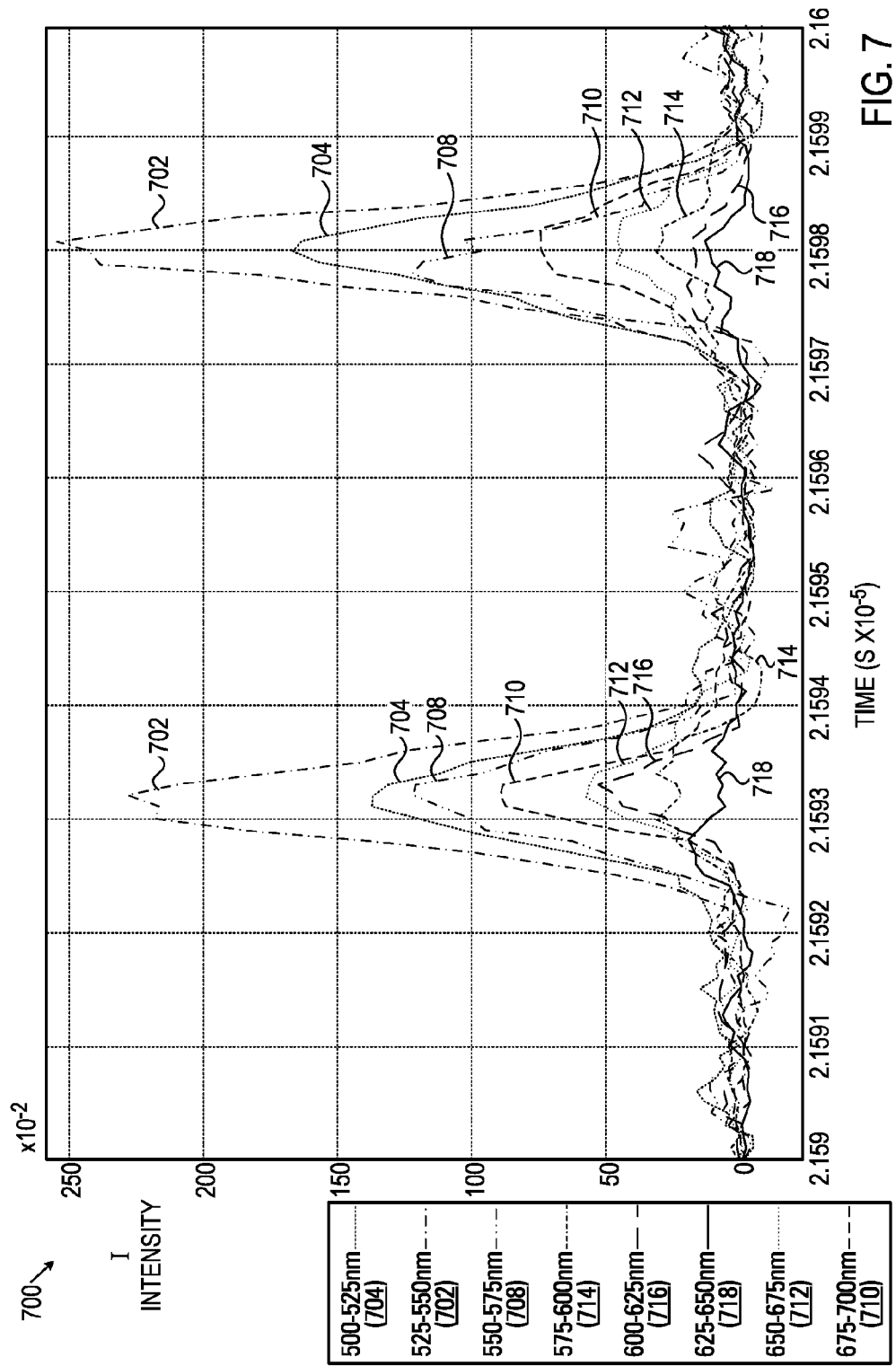
Figure 8:
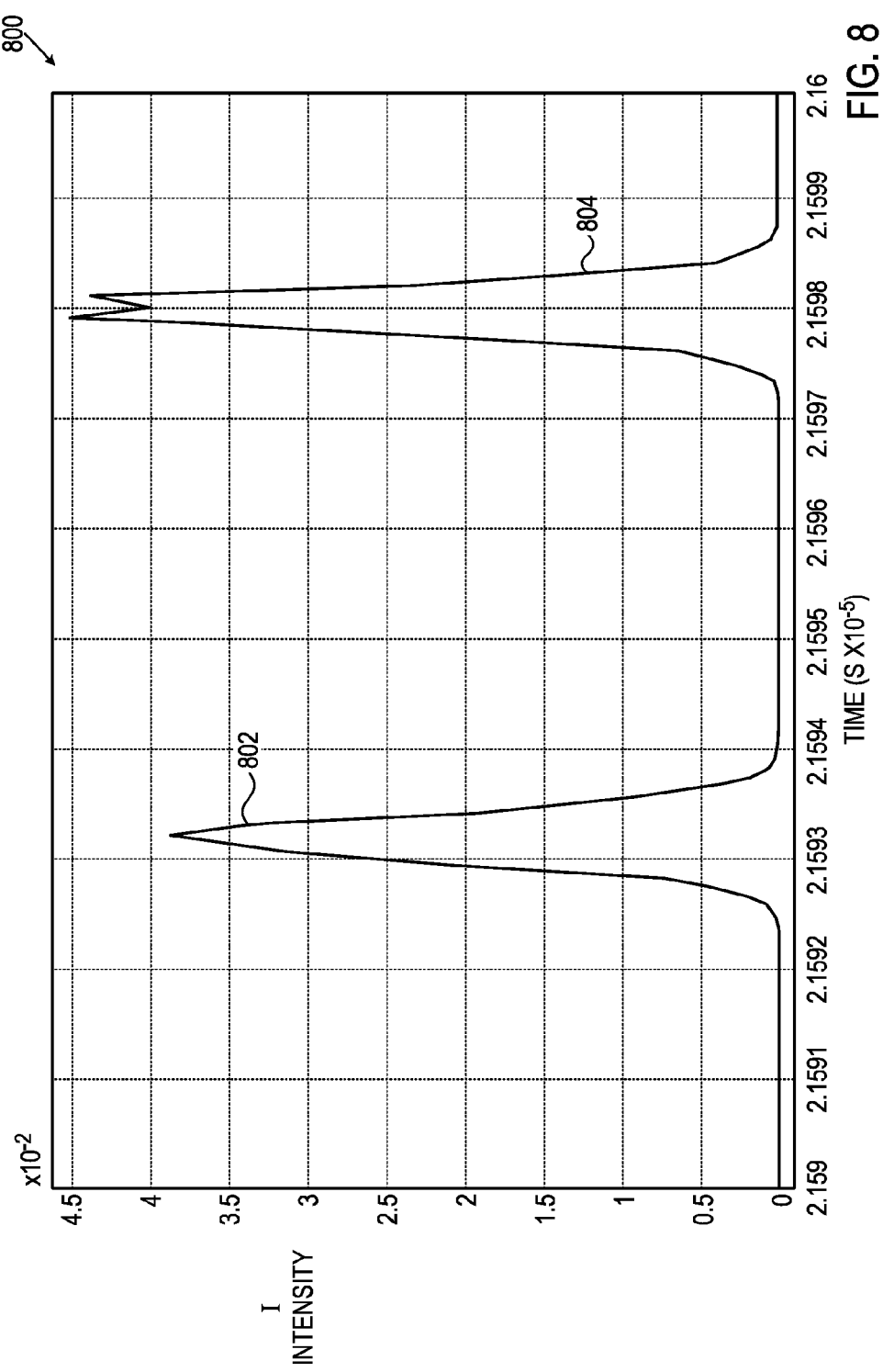
Figure 9:
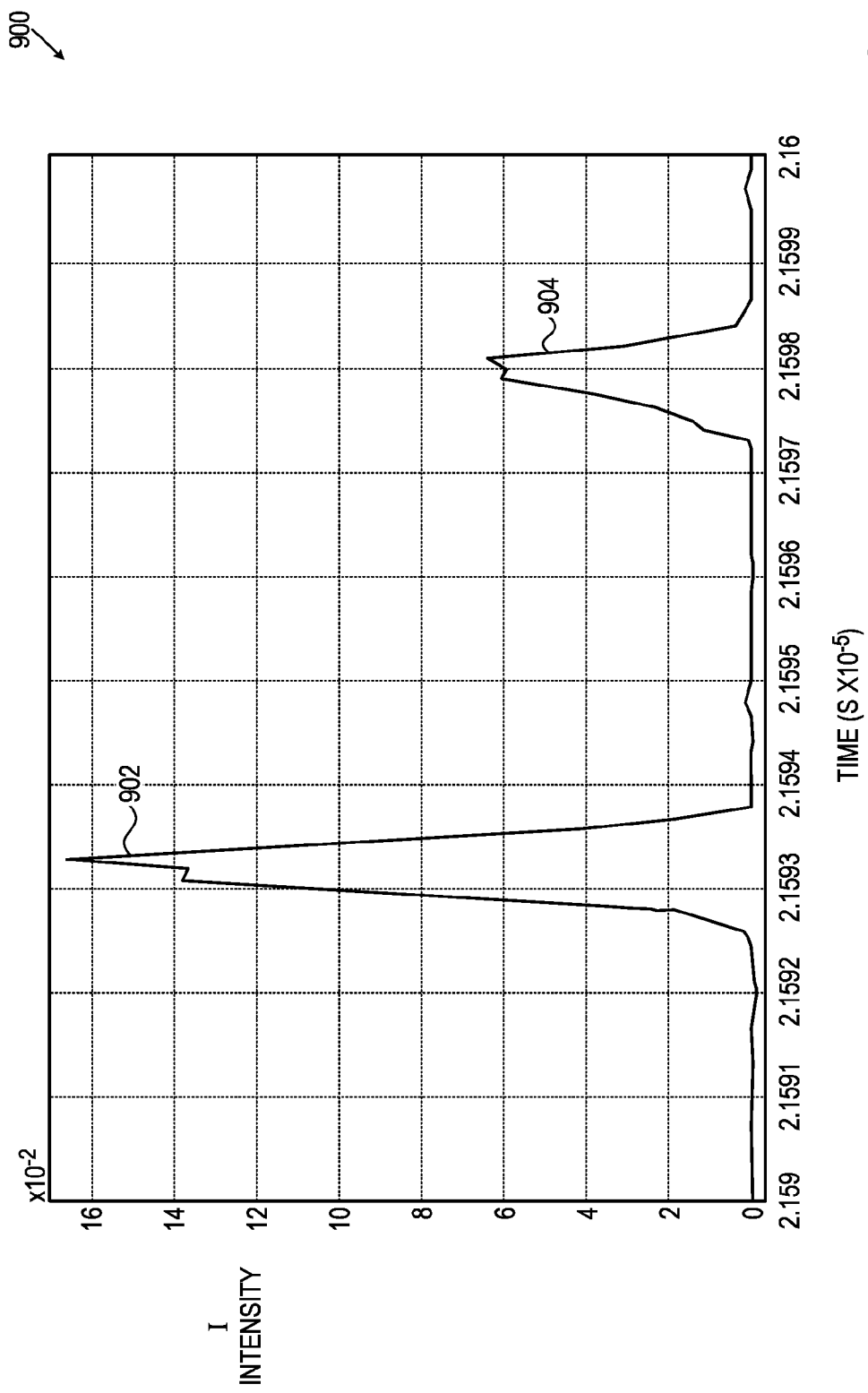
Figure 10:
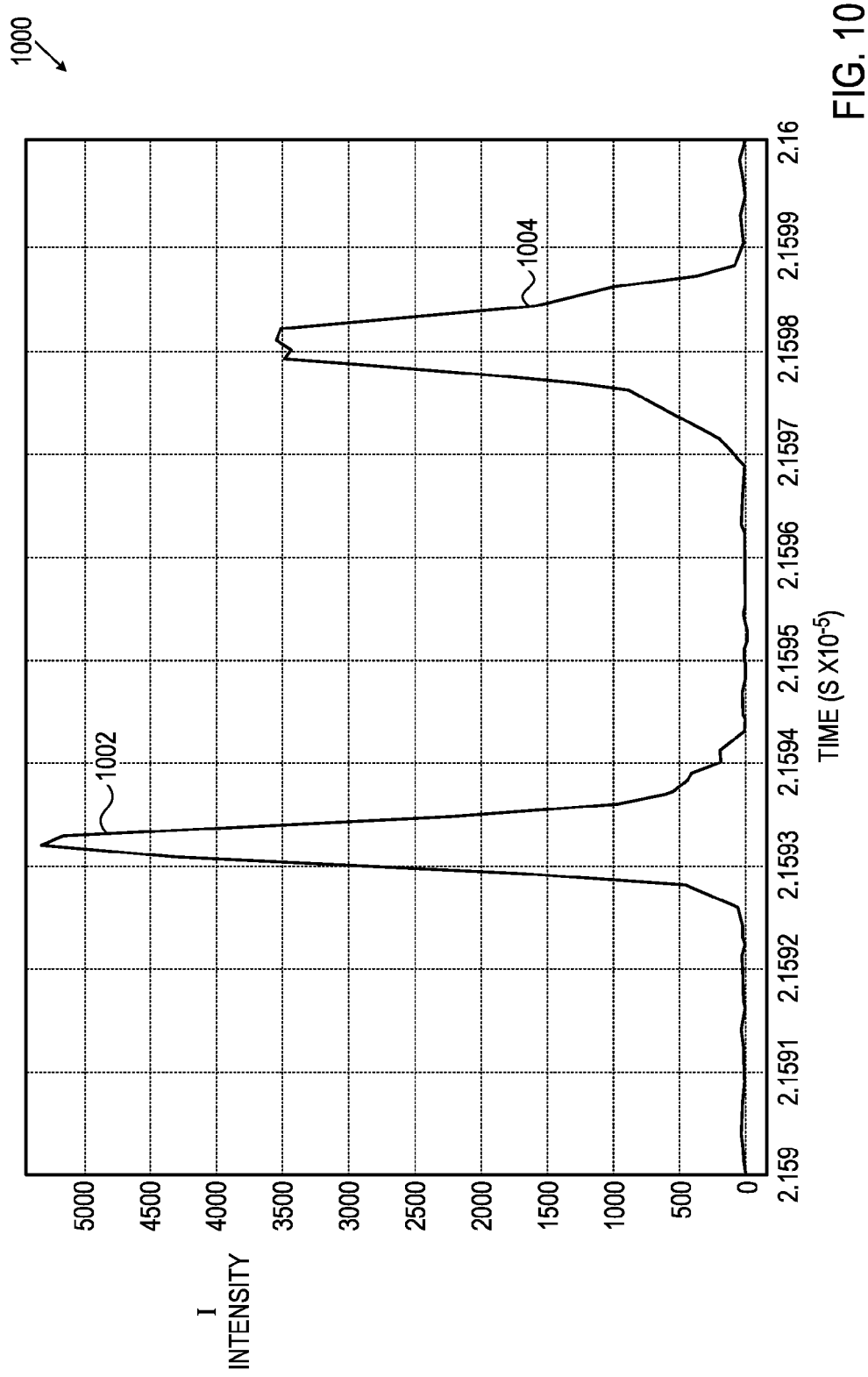

FIG. 9 is a graphical output of data from FIG. 7 after a second mathematical manipulation, in accordance with an embodiment of the present invention;

FIG. 10 is a graphical output of data from FIG. 7 after a third mathematical manipulation, in accordance with an embodiment of the present invention; and FIG. 11 is a graphical output of an event locator, based on data from FIG. 8-10, in accordance with an embodiment of the present invention.

In all the figures similar reference numerals identify similar parts.

DETAILED DESCRIPTION OF THE INVENTION

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

International patent application publication no. WO2011/128893 to Kasdan et al., describes a device, system and method for rapid determination of a medical condition and is incorporated herein by reference.

The microfluidic cartridges of the present invention may be any suitable cartridge as shown in the figures or any of the prior art cartridges described or cited herein, such as, but not limited to, those described in U.S. Pat. No. D669,191 S1, US20120266986 A1, EP1846159 A2, US2012275972, WO11094577A, US2007292941A and EP1263533 B1.

Figure 1:
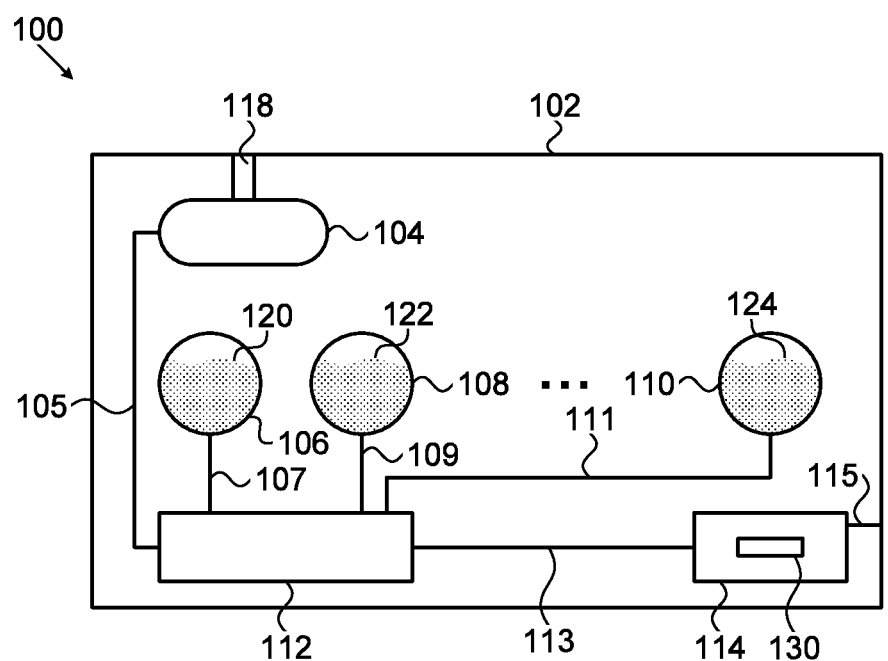

Reference is now made to FIG. 1, which is a simplified schematic illustration showing an apparatus 100 for detecting a biological condition, in accordance with an embodiment of the present invention.

Apparatus 100 is a kit comprising a cartridge 102 and a number of chemical/biochemical reactants termed herein, treatment compositions. The treatment compositions are adapted to react, at least in part, with biological specimen, such as a body specimen, to be introduced to the apparatus. The body specimen may be a bodily fluid such as, but not limited to, blood, serum, plasma, urine, saliva, cerebrospinal fluid (CSF), serous fluid, peritoneal fluid and synovial fluid. Additionally or alternatively, the body specimen may be a solid such as a hair, a tooth part, a bone part or a piece of cartilage.

Apparatus 100 comprises a specimen receiving element 118, adapted to transfer the specimen to a sample composition chamber 104. The sample composition chamber comprises on or more transfer elements 105, adapted to transfer the specimen from the sample composition chamber to one or more other locations in the cartridge. In the non-limiting example shown in FIG. 1, transfer element 105 is a conduit in fluid connection with a treatment chamber 112.

Additionally, the cartridge comprises a number of treatment composition chambers 106, 108, 110, adapted to respectively house a corresponding number of treatment compositions 120, 122, 124. These treatment compositions may be liquid, solid or combinations thereof. Apparatus 100 is typically sold commercially as a kit with the treatment compositions disposed therein. In some cases, the apparatus 100 may be adapted for a one-off test and may be disposable. In other cases, the apparatus may be re-used. A re-usable apparatus may be adapted to receive additional external compositions (not shown) or may have a plurality of treatment compositions, wherein only a portion is used for each test.

The apparatus may be constructed and configured such that the treatment composition comprises proteins attached to a surface, such as to beads. A plurality of beads or other structural elements with proteins attached to their surfaces can be made by any one or more of the following methodologies: —
- simple attachment such as by adsorption via electrostatic or hydrophobic interactions with the surface, entrapment in immobilized polymers, etc.
- non-covalent or physical attachment;
- covalent bonding of the protein to the bead surface
- biological recognition (e. g., biotin/streptavidin).
- requires two steps: a first layer is formed by silane chemistry such that the surface presents a reactive group (e. g., epoxy, amino, thiol, etc.), and a second layer (e. g., the protein to be immobilized or a linker molecule) is covalently attached via the immobilized reactive groups.
- covalent attachment to functionalized polymer coatings on the interior of the device or linkage to the free end of a self-assembled monolayer (SAM) on a gold surface.

The reaction type may include any one or more of antigen-antibody binding, sandwich (such as antibody—antigen-antibody), physical entrapment, receptor-ligand, enzyme-substrate, protein-protein, aptamers, covalent bonding or biorecognition.

Cartridge 102 further comprises at least one transfer element 107, 109, 111 in fluid communication with each respective of treatment composition chamber, each transfer element also being in fluid communication with treatment chamber 112. These elements are typically microfluidic channels and may be designed for mixing, such as being tortuous in shape.

Various methodologies for transferring the contents of the treatment composition chambers and the sample composition chamber via the transfer elements to the treatment chamber may be employed, some of which are known in microfluidics technologies. These include air blowing, suction, vacuuming, mechanical transfer, pumping and the like.

Cartridge 102 further comprises at least one transfer element 113 in fluid communication with treatment chamber 112 and with an evaluation chamber 114.

Optionally, evaluation chamber 114 is further in fluid communication with a transfer element 115, adapted to remove the contents of the evaluation chamber for disposal outside the cartridge. Alternatively, the evaluation chamber may have no external disposal means.

Table 1 shows some representative applications of apparatus 100 and methods of the present invention.

TABLE 1

Applications of the apparatus and methods of this invention.

| Application | Type of Test | Relevant Figures in this invention | Typical Prior Art Laboratory Turnaround time (TAT)- see references | This invention Turnaround time (TAT) | References |
|---|---|---|---|---|---|
| Application #1 - CD64 Infection & Sepsis | Surface Marker | FIGS. 1-2 and 3-5D | 4 hours | 10 minutes | U.S. Pat. No. 8,116,984, Davis, BH et al., (2006) |
| 1 - Fetal Hemoglobin Test | Plasma Protein | FIGS. 1-2 and 6-8D | 4 hours | 10 minutes | Dziegiel et al. (2006) |
| 2 - Low Platelet Count | Surface Marker | FIGS. 1-2 and 3-5D | 4 hours | 10 minutes | Segal, H. C., et al. (2005): |
| 3 - Resolving BLAST Flag for hematology Lab | Surface Marker | FIGS. 1-2 and 3-5D | 4 hours | 10 minutes | Guerti, K., et al. |
| 4 - CD34 Stem Cell Enumeration Assay | Surface Marker | FIGS. 1-2 and 3-5D | 4 hours | 10 minutes | Sutherland et al. (1996) |
| 5 - Platelets Activation Assay CD62 | Surface Marker | FIGS. 1-2 and 3-5D | 4 hours | 10 minutes | Graff et al. (2002) Divers, S. G., et al. (2003) |
| 6 - D-dimer (Bead based protein) | Plasma Protein | FIGS. 1-2 and 6-8D | 4 hours | 10 minutes | Stein et al. (2004) Rylatt, D. B., et al. (1983): |
| 7 - Chorioamnioitis CD64 | Surface Marker | FIGS. 1-2 and 3-5D | 4 hours | 10 minutes | Hillier et al. (1988) |
| 8 - CD20 Cell Quantitation (Therapy Monitoring) | Surface Marker | FIGS. 1-2 and 3-5D | 4 hours | 10 minutes | Rawstron et al. (2001) Cheson et al. (1996) |
| 9 - CD52 Cell quantitation (Therapy Monitoring) | Surface Marker | FIGS. 1-2 and 3-5D | 4 hours | 10 minutes | Rawstron et al. (2001) |
| 10 - Circulating Tumor Cells | Surface Marker | FIGS. 1-2 and 3-5D | 4 hours | 10 minutes | Cristofanilli et al. (2004 |
| 11 - Reticulated Platelet Assay | Surface Marker | FIGS. 1-2 and 3-5D | 4 hours | 10 minutes | Matic et al. (1998) Ault et al (1993) Wang et al. (2002) |
| 12 - Bacteria Detection in platelet packs | | | 4 hours | 10 minutes | Blajchman et al (2005) McDonald et al. (2005) |
| 13 - Platelet Associated Antibodies | Surface Marker | FIGS. 1-2 and 3-5D | 4 hours | 10 minutes | Michelson (1996) |
| 14 - Residual Leukocyte Count in blood products | Surface Marker | FIGS. 1-2 and 3-5D | 4 hours | 10 minutes | Bodensteiner, (2003) |
| 15 - CD4 HIV AIDS | Surface Marker | FIGS. 1-2 and 3-5D | 4 hours | 10 minutes | Rodriguez (2005). Dieye et al. (2005) |

TABLE 1-continued

Applications of the apparatus and methods of this invention.

| Application | Type of Test | Relevant Figures in this invention | Typical Prior Art Laboratory Turnaround time (TAT)- see references | This invention Turnaround time (TAT) | References |
|---|---|---|---|---|---|
| 16 - Leukemia Panels - Very complex | Surface Marker | FIGS. 1-2 and 3-5D | 4 hours | 10 minutes | Drexler et al (1986) |
| 17 - Bladder Cancer Screening in Urine - Urine sample | Surface Marker | FIGS. 1-2 and 3-5D | 4 hours | 10 minutes | Ramakumar et al (1999) Lotan et al. (2009) |
| 18 - HLA DR Sepsis and Immunosuppression | Surface Marker | FIGS. 1-2 and 3-5D | 4 hours | 10 minutes | Hershman et al. (2005) Perry et al (2003) |
| 19 - RECAF Protein for Canine and other Cancers | Plasma Protein | FIGS. 1-2 and 6-8D | 4 hours | 10 minutes | Moro et al. (2005). |
| 20 - CytoImmun - Cervical Screening | | | 4 hours | 10 minutes | Hilfrich et al. (2008) |
| 21 - Procalcitonin (Bead Based Protein) + Feasibility | Plasma Protein | FIGS. 1-2 and 6-8D | 4 hours | 10 minutes | Assicot et al. (1993) Christ-Crain et al. (2004) |

Figure 2:
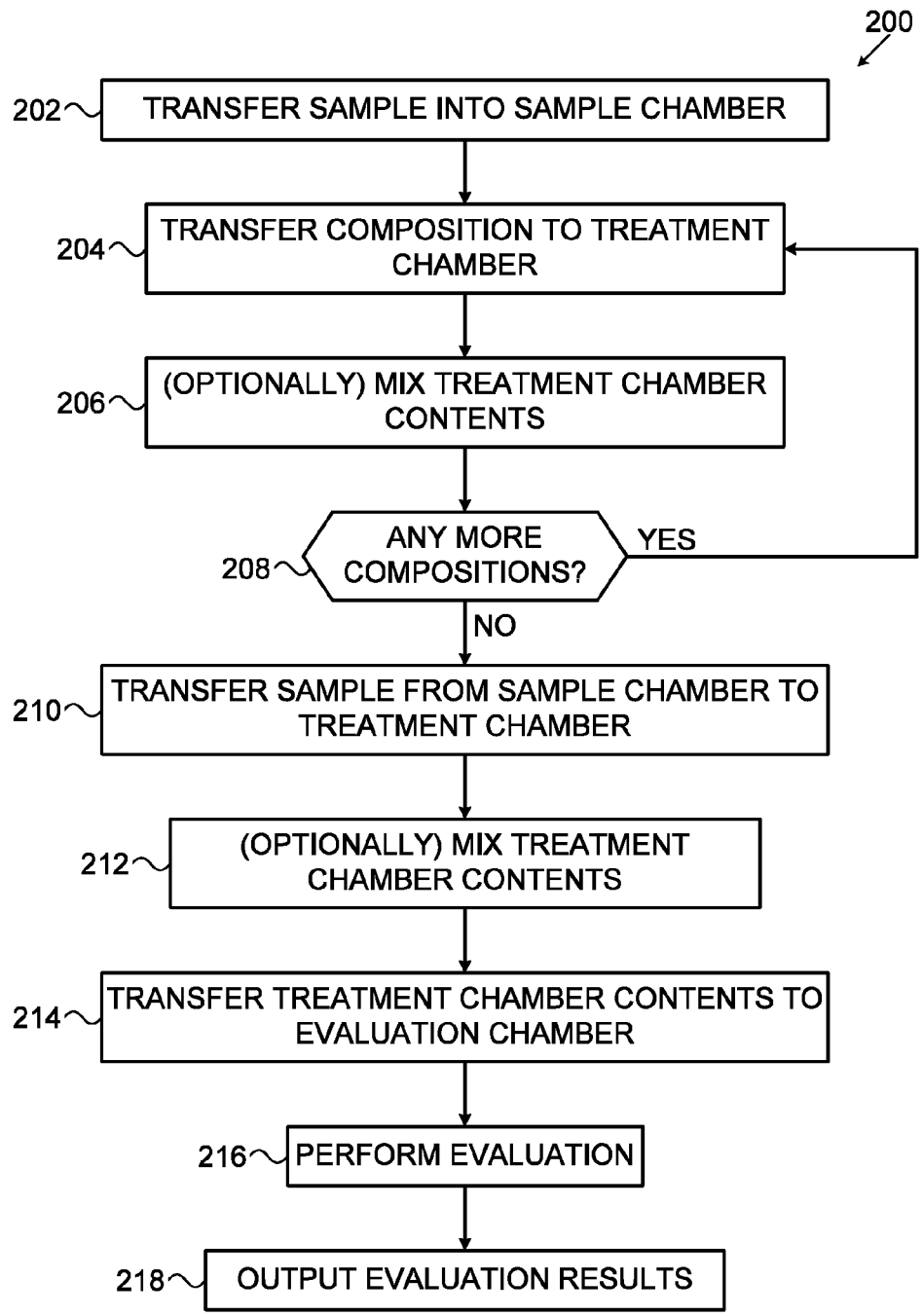

Reference is now made to FIG. 2, which is a simplified flow chart 200 of a method for detecting a biological condition, in accordance with an embodiment of the present invention.

It should be understood that each of the steps of the method may take a predetermined period of time to perform, and in between these steps there may be incubation and/or waiting steps, which are not shown for the sake of simplicity.

In a sample transferring step 202, a sample, such as a bodily specimen is transferred from outside apparatus 100 via receiving element 118 into sample composition chamber 104 and then to the treatment chamber 112. According to some embodiments, the volume of the specimen or sample is less than 200 µL, less than 100 µL, less than 50 µL, less than 25 µL or less than 11 µL.

Thereafter, treatment composition 120 is transferred via transfer element 107 to the treatment chamber in a composition transfer step 204. In some cases, there may be a treatment composition disposed in the treatment chamber.

Depending on the nature of the treatment composition and sample/specimen type, there may be a requirement to mix or agitate the treatment chamber contents in an optional mixing step 206. This may be performed by using a small stirbar (not shown) disposed in the chamber. Additionally or alternatively, this may be effected by the fluid dynamics of kit. Additionally or alternatively, stirbars may be disposed in any of the other chambers in the apparatus.

Typically, the total sample volumes are in the range of 10 to 1000 µL, 100 to 900 µL, 200 to 800 µL, 300 to 700 µL, 400 to 600 µL, or 420 to 500 µL.

According to some embodiments, the volume of the treatment composition chambers 106, 108, 110 (also called blisters) is from about 1 µL to 1000 µL. According to other embodiments, the volume of the specimen is from about 10 µL to 200 µL. According to other embodiments, the volume of the specimen is about 1, 10, 20, 30, 40, 50, 60, 70, 80, 90, 100, 120, 140, 160, 180, 200, 250, 300, 350, 400, 450, or 500 µL.

According to some embodiments, the volume of the treatment compositions 120, 122, 124 is at most about 500 µL. According to other embodiments, the volume of the specimen is at most about 200 µL. According to other embodiments, the volume of the specimen at most about 500, 450, 400, 350, 300, 250, 200, 180, 160, 140, 120, 100, 90, 80, 70, 60, 50, 40, 30, 20, 10, or 1 µL.

According to some embodiments, the volume of a reactant is at least about 1 µL. According to other embodiments, the volume of the specimen is from about 10 µL. According to other embodiments, the volume of the specimen is at least about 1, 10, 20, 30, 40, 50, 60, 70, 80, 90, 100, 120, 140, 160, 180, 200, 250, 300, 350, 400, 450, or 500 µL.

The sequence of transfer of the various treatment compositions may be important to the reaction sequence and is typically predefined. Steps 204-206 may be performed, for example on treatment composition chamber 106, thereafter on treatment composition chamber 108 and thereafter on treatment composition chamber 110. In some cases, some of these steps may be performed concurrently.

In a checking step 208, it is ascertained whether all the compositions required for the sample treatment have been transferred to the treatment chamber. If any compositions remain, then steps 204-206 are performed on the subsequent treatment composition chamber(s). If no further treatment compositions require transfer, then the sample/specimen is transferred from chamber 104 into the treatment chamber.

Thereafter, in a second sample transfer step 210, the sample is transferred from the sample composition chamber into the treatment chamber.

According to some embodiments, step 210 may be performed before steps 204-208. If required, an optional mixing step 212 to the contents of the treatment chamber may be performed.

In a transferring step 214, the contents of the treatment chamber are transferred to the evaluation chamber.

The evaluation chamber 114 is configured and constructed for one or more evaluation steps 216. These may include any of the following, or combinations thereof:
a) transfer of radiation there-through,
b) impinging radiation thereupon;
c) detecting reflected, refracted, and/or transmitted radiation,
d) detecting emitted radiation;
e) capturing one or more images thereof;
f) performing image analysis on the captured images;
g) measuring electrical characteristics of the treated specimen;
h) impinging sonic energy thereon;
i) detecting sonic energy therefrom; and j) analyzing the outputs of any one or more of the above steps.

According to some embodiments, the cartridge is introduced into a system as described in International patent application publication no. WO2011/128893 to Kasdan et al., incorporated herein by reference.

The results of the evaluation step are then outputted in a results outputting step 218.

According to some embodiments; the apparatus may have on-board means for showing a result, such as a colorimetric strip (not shown). Additionally or alternatively, the results are displayed in a display unit, separate and remote from apparatus 100.

Figure 3:
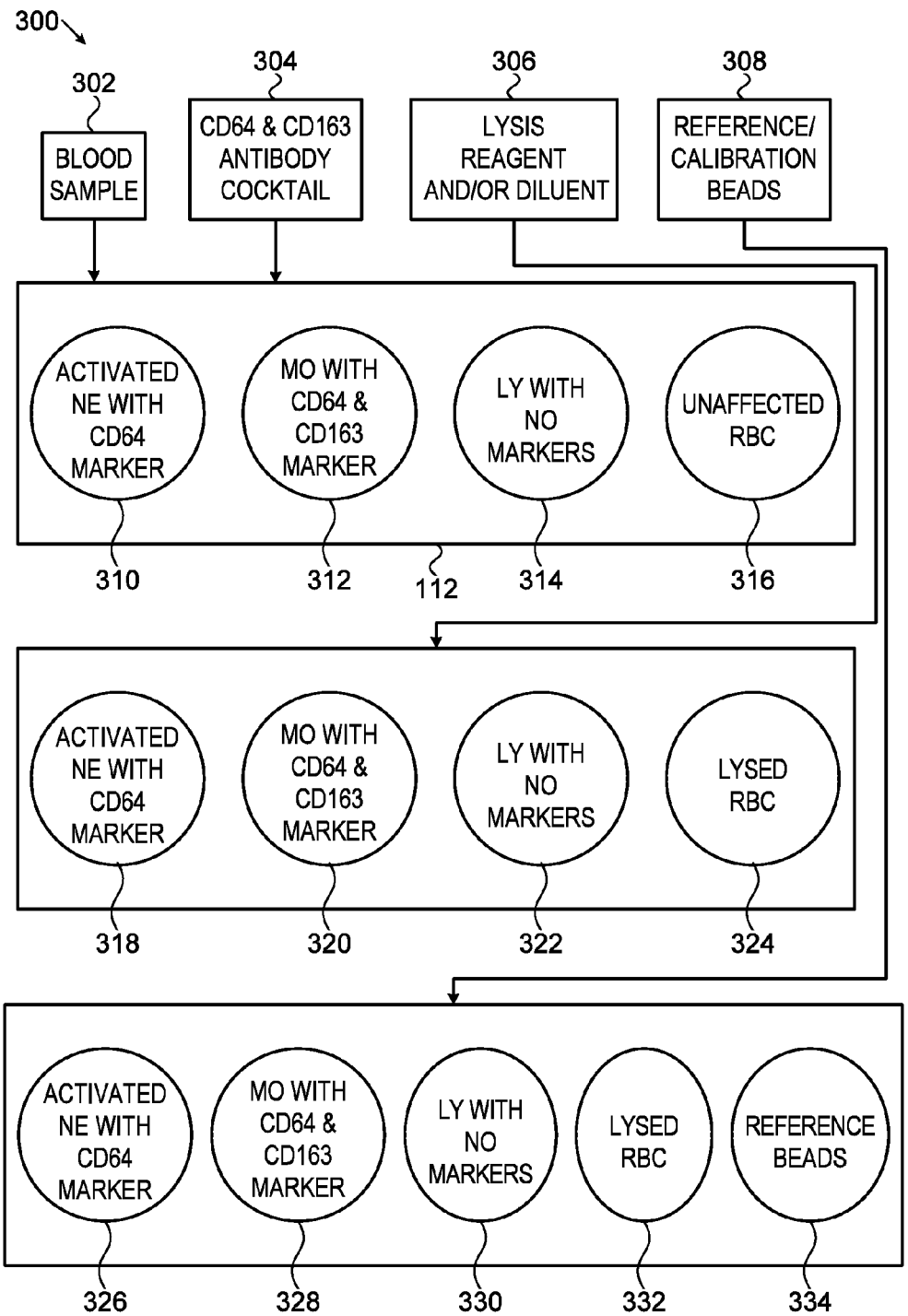

Reference is now made to FIG. 3, which is a simplified schematic illustration showing a methodology 300 for detecting a biological condition associated with a CD64 cell surface antigen, in accordance with an embodiment of the present invention.

According to some embodiments, the method is carried out in the apparatus shown in FIG. 1 and as described herein. A biological specimen, such as a blood sample, is aspirated via specimen receiving element 118 to sample composition chamber 104, and then to treatment chamber 112. The sample is typically of a volume in the range of 10-200 μL.

The blood sample is typically whole blood recently removed from a patient. The whole blood comprises mainly red blood cells (also called RBCs or erythrocytes), platelets and white blood cells (also called leukocytes), including lymphocytes and neutrophils. Increased number of neutrophils, especially activated neutrophils are normally found in the blood stream during the beginning (acute) phase of inflammation, particularly as a result of bacterial infection, environmental exposure and some cancers.

A cocktail 304 comprising antibodies to CD64 and antibodies to CD163 is introduced to the treatment chamber (see Davis et al. (2006)). Each antibody type is typically tagged by a specific fluorescent tag.

The contents of the chamber are incubated and/or mixed as is required to bind the activated blood neutrophils with the CD64 tagged antibody (also called a marker) to form activated neutrophils with CD64 marker 310, and/or monocyte with a CD64 tagged antibody and a CD163 tagged antibody 312. Lymphocytes with no markers 314 are present in the contents, as well as unaffected RBCs 316.

Thereafter, a lysis reagent or diluent 306 is introduced into treatment chamber 112. In the case of a lysis reagent, it is adapted to lyse red blood cells to form lysed red blood cells 324. Additionally, reference/calibration beads 308 are added to the treatment chamber. These are used to calibrate the outputs, as is explained with reference to FIGS. 5A-5D hereinbelow.

CD64 (Cluster of Differentiation 64) is a type of integral membrane glycoprotein known as an Fc receptor that binds monomeric IgG-type antibodies with high affinity. Neutrophil CD64 expression quantification provides improved diagnostic detection of infection/sepsis compared with the standard diagnostic tests used in current medical practice.

CD163 (Cluster of Differentiation 163) is a human protein encoded by the CD163 gene. It has also been shown to mark cells of monocyte/macrophage lineage.

Figure 4:
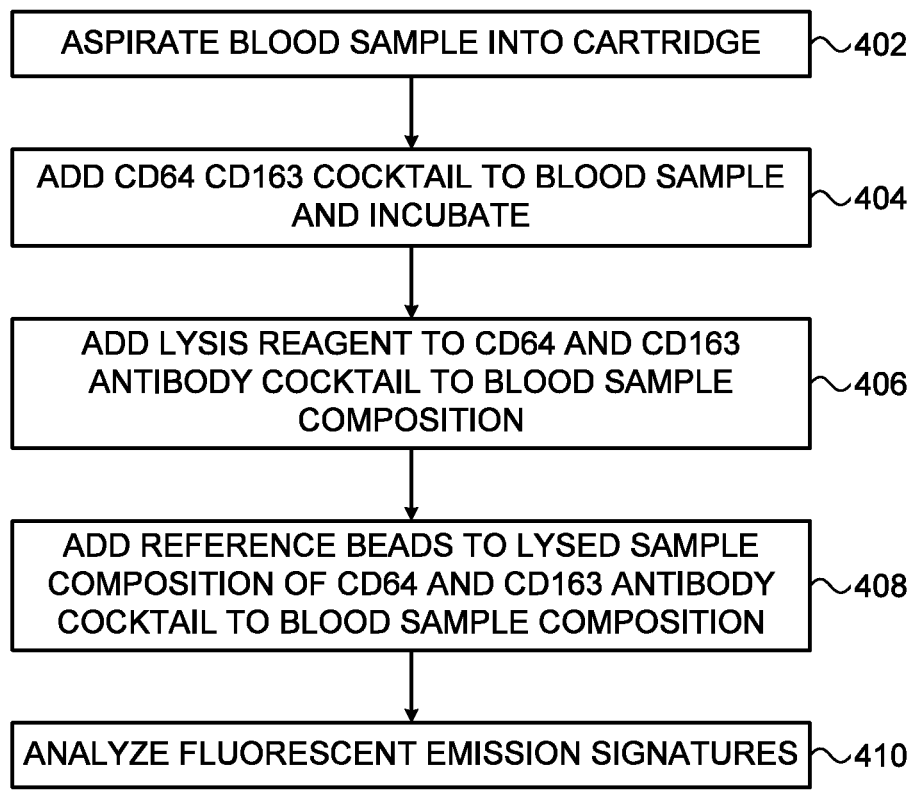

Reference is now made to FIG. 4, which is a simplified flow chart 400 of a method for detecting a biological condition associated with a CD64 cell surface antigen, in accordance with an embodiment of the present invention.

According to some embodiments, the method is carried out in the apparatus shown in FIG. 1 and as described herein. In a first transferring step 402, a biological specimen, such as a blood sample is aspirated via specimen receiving element 118 to sample composition chamber 104. The sample is typically of a volume in the range of 10-200 μL.

Typically, the total sample volumes are in the range of 10 to 1000 μL, 100 to 900 μL, 200 to 800 μL, 300 to 700 μL, 400 to 600 μL, or 420 to 500 μL.

According to some embodiments, the volume of the treatment composition chambers 106, 108, 110 (also called blisters) is from about 1 μL to 1000 μL. According to other embodiments, the volume of the specimen is from about 10 μL to 200 μL. According to other embodiments, the volume of the specimen is about 1, 10, 20, 30, 40, 50, 60, 70, 80, 90, 100, 120, 140, 160, 180, 200, 250, 300, 350, 400, 450, or 500 μL.

According to some embodiments, the volume of the treatment compositions 120, 122, 124 is at most about 500 μL. According to other embodiments, the volume of the specimen is at most about 200 μL. According to other embodiments, the volume of the specimen at most about 500, 450, 400, 350, 300, 250, 200, 180, 160, 140, 120, 100, 90, 80, 70, 60, 50, 40, 30, 20, 10, or 1 μL.

According to some embodiments, the volume of a reactant is at least about 1 μL. According to other embodiments, the volume of the specimen is from about 10 μL. According to other embodiments, the volume of the specimen is at least about 1, 10, 20, 30, 40, 50, 60, 70, 80, 90, 100, 120, 140, 160, 180, 200, 250, 300, 350, 400, 450, or 500 μL.

In an addition step 404, a cocktail of tagged antibodies to CD64 and to CD163 is added to the treatment chamber 112 and is incubated with the blood sample. In the incubation phase of this step, the antibodies bind activated neutrophils with CD64 marker 310, and/or monocytes activated with a CD64 tagged antibody and a CD163 tagged antibody 312.

In a lysis reagent addition step 406, the lysis reagent is added to the treatment chamber and thereby lyses at least some of the RBCs in the chamber.

At any suitable time, typically following lysis step 406, reference beads are added to the contents of the treatment chamber in a reference bead adding step 408.

After a predefined period of time, an analysis step 410 is performed to analyze the fluorescent emission signatures from the contents. This is described in further detail with reference to FIGS. 5A-5D. According to some examples, the evaluation chamber 114 is constructed and configured to allow cells to pass through a reading zone 130 such that each cell passing therethrough is analyzed individually. The assay sensitivity is around 86% and its specificity is around 87% (Hoffmann, 2011).

The time required to complete an assay using apparatus 100 of the present invention varies depending on a number of factors, with non-limiting examples that include described herein. In some embodiments, the time required to complete an assay is from about 0.5 to 100 minutes. In other embodiments, the time required to complete an assay is from about 1 to 20 minutes. In still other embodiments, the time required to complete an assay is from about 1 to 10 minutes. In some examples, the time required to complete an assay is from about 1, 2, 3, 4, 5, 6, 7, 8, 9, 10, 15, 20, 25, 30, 35, 40, 50, 60, 80, or 100 minutes.

Figure 5A:
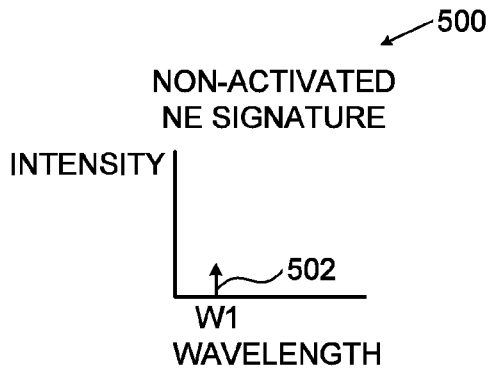

Reference is now made to FIG. 5A, which is a graphical output of a fluorescent detection assay of a non-activated neutrophil signature 500 associated with the method of FIGS. 3-4, in accordance with an embodiment of the present invention. The non-activated tagged neutrophils each emit a signal 502 at wavelength W1 of an intensity I1. The wavelengths shown in FIGS. 5A-5D represent a peak wavelength of waveband outputs detected, as are shown in FIGS. 7-11.

Figure 5B:
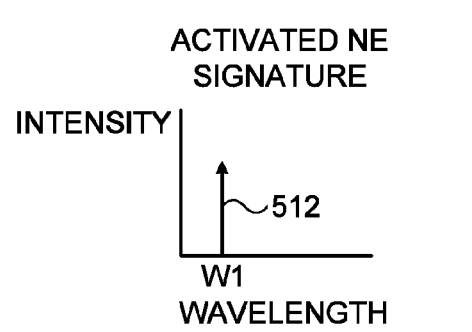

FIG. 5B shows a graphical output of a fluorescent detection assay of an activated neutrophil signature 510, associated with the method of FIGS. 3-4, in accordance with an embodiment of the present invention. Each activated tagged neutrophil emits an activated neutrophil signature 512 at wavelength W1 of an intensity I2. Typically I2 is greater than I1. In some cases the difference in signatures 512 and 510 may be detected by an image analysis, a fluorescent emission radiation count or by other qualitative or quantitative methods known in the art. The current example is not meant to be limiting.

Figure 5C:
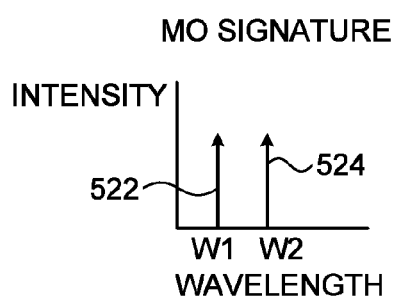

Turning to FIG. 5C, there can be seen a graphical output of a fluorescent detection assay of a monocyte signature 520, associated with the method of FIGS. 3-4, in accordance with an embodiment of the present invention. The monocyte signature comprises a first signal 522 at a first wavelength W1 of an intensity I3 and a second signal 524 at a second wavelength W2 of an intensity I4.

Figure 5D:
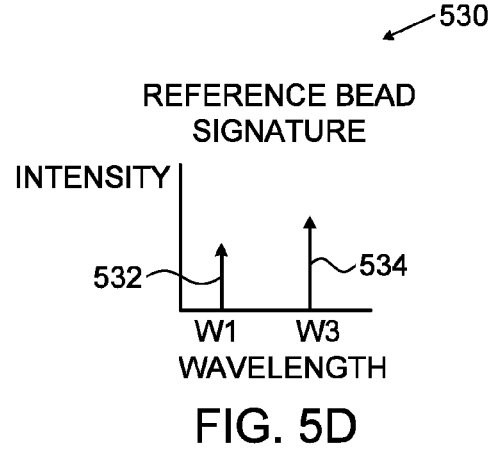

FIG. 5D shows a graphical output of a fluorescent detection assay of a reference bead signature 530, associated with the method of FIGS. 3-4, in accordance with an embodiment of the present invention. The reference bead signature comprises a first signal 532 at a first wavelength W1 of an intensity I1 (similar or equal to non-activated tagged neutrophils' signal 502) and a second signal 534 at a second wavelength W3 of an intensity IS.

This methodology enables the identification and quantification of activated neutrophils by intensity of signature 512 of the CD64 tag. Monocytes are identified by the double signal signature 522, 524, acting as a positive control. Reference beads are identified by the unique signal 534 at wavelength W3. The intensity of signal 532 at wavelength W1 provides a reference level of CD64 for the comparison of intensity of 512 of the neutrophils.

Lymphocytes with no markers 330 (FIG. 3) act as a negative control and should provide no fluor signature, but may be detected by their scattering or other characteristics. Further details of some embodiment of this assay procedure are described in U.S. Pat. No. 8,116,984 and in Davis, B H et al., (2006).

Figure 6:
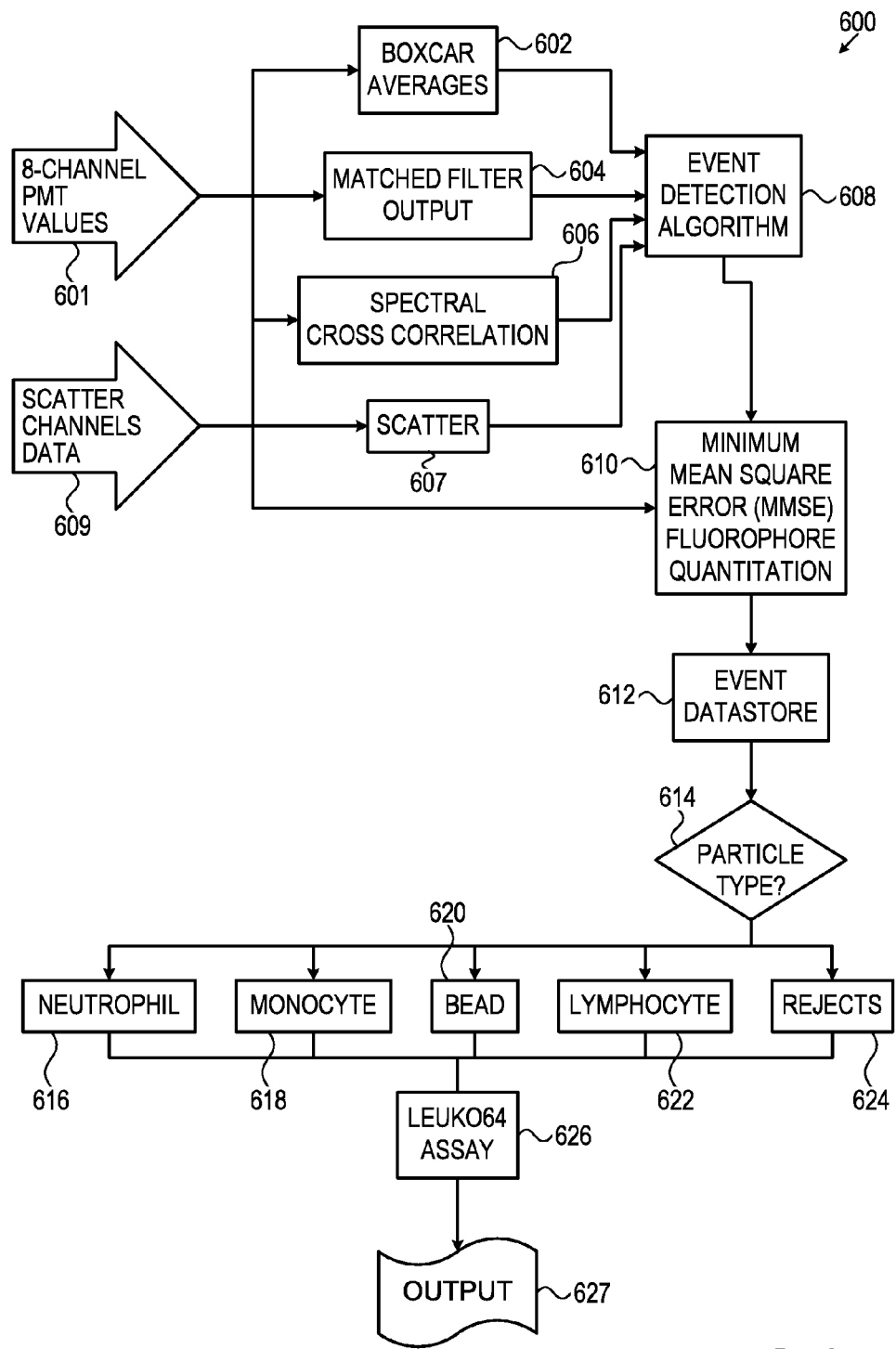

Reference is now made to FIG. 6, which is a simplified flow chart of a method 600 for differentiating between different particles, in accordance with an embodiment of the present invention.

The input to the processing is a time series from each of the channels in the eight channel photomultiplier array 601. In addition, data from multiple scatter channels 609 is introduced. Each fluorescent time series and scatter time series may be processed individually employing respective spectral crosscorrelation algorithm 606 and scatter algorithm 607 to smooth it and minimize noise. Two possible processing methods are boxcar averaging algorithm 602 and matched filtering algorithm 604. In addition, groups of individual channels may be correlated to yield a multiple spectral crosscorrelations 606. One or more of these derived time series may be used to determine event locations.

Once an event is located in the eight channel time series the composition of that event in terms of known fluorophore signatures is determined using a minimum mean square error fit 610. The event is now described in terms of its composition of known fluors. Each event thus described is stored in an event store, i.e. memory, together with the data from the eight time series for that event and its description 612. Based on the fluor composition for each event in the data store, it is possible to determine the type of particle. For example, a neutrophil 616 is characterized by the single fluor attached to the CD64 antibody shown in FIG. 5 as W1. Thus events that are preponderantly characterized by the single fluor attached to the CD64 antibody are identified as neutrophils.

Similarly, monocytes 618 are characterized by fluors W1 and W2 so that an event with both of these fluor signatures is identified as a monocyte. Similarly, a bead 620 is characterized by an event that has fluors W1 and W3. Lymphocytes 622 do not express significant fluorescence but are identified by their scatter as events. Events that do not match any of the known combinations of the fluorophores are identified as rejects 626.

Given the population of identified events, the median intensity of the neutrophil population and the median intensity of the bead population are determined. The ratio of the neutrophil median to the bead median is the desired Leuko64 index. The positive control value is determined as the median intensity of the CD64 fluorophore bound to monocytes divided by the median intensity of the same fluorophore on the bead population. The negative control value is determined by the median intensity of the CD64 fluorophore bound to lymphocytes. These are the key steps in performing the Leuko64 assay.

FIG. 7 is a graphical output 700 of fluorescence from reference beads in eight wavebands, in accordance with an embodiment of the present invention. This figure shows the smoothed signals from the eight channel PMT array for two reference beads. The amplitude for each waveband is shown on the same graph. The corresponding wavelength range is shown for each plot 702, 706, 708, 710, 712, 714, 716, 718 in the legend box. The two fluorophores signatures present in this plot are 702, 706 and 708 for FITC, which is the fluorophore attached to the CD64 antibody and 710, 712 for Starfire Red, which is the fluorophore identifying the reference beads.

Reference is now made to FIG. 8, which is a graphical output 800 of data from FIG. 7 after a first mathematical manipulation, in accordance with an embodiment of the present invention. FIG. 8 shows the cross correlation of wave bands one two and three corresponding to wavelength 500 to 525, 525 to 550, and 552 to 575 nm. This cross correlation is computed by multiplying the boxcar smoothed time series corresponding to these wavelengths. This signal will have a high-value when an event containing the FITC fluorophore is present.

FIG. 9 is a graphical output 900 of data from FIG. 7 after a second mathematical manipulation, in accordance with an embodiment of the present invention. FIG. 9 shows the cross correlation of wave bands 3, 4 and 5 corresponding to wavelengths 550 to 575, 575 to 600, and 600 to 625 nm. This signal will have a high-value when an event containing the PE fluorophore is present.

FIG. 10 is a graphical output 1000 of data from FIG. 7 after a third mathematical manipulation, in accordance with an embodiment of the present invention. FIG. 10 shows the cross correlation of wave bands 7 and 8 corresponding to wavelengths 650 to 675, and 675 to 700 nm. This signal will have a high-value when an event containing the Starfire Red fluorophore is present.

FIG. 11 is a graphical output 1100 of an event locator, based on data from FIG. 8-10, in accordance with an embodiment of the present invention. FIG. 11 shows the event locations determined from the cross correlations computed in FIGS. 8, 9 and 10. The solid fill area 1102 corresponds to the region where any of the cross correlations 802, 902 and 1002 exceeded a predefined threshold. Similarly, the solid fill area 1104 corresponds to the region where any of the cross correlations 804, 904 and 1004 exceeded a predefined threshold. This then completes the event location process.

Example

Application No. 1

CD64 Infection & Sepsis

A cartridge 102 (FIG. 1) is prepared for receiving a blood sample. The cartridge comprises a number of treatment composition chambers 106, 108, 110, adapted to respectively house a corresponding number of treatment compositions 120, 122, 124. These compositions are described in further detail in U.S. Pat. No. 8,116,984 and in Davis, B H et al., (2006)), incorporated herein by reference. In brief, Reagent A comprises a mixture of murine monoclonal antibodies (contains buffered saline), Reagent B—10× Concentrated Trillium Lyse solution (contains ammonium chloride), Reagent C—suspension of 5.2 μm polystyrene beads labeled with Starfire Red and fluorescein isothiocyanate (FITC), (contains <0.1% sodium azide and 0.01% Tween 20).

In a sample transferring step 202 (FIG. 2), a 10 uL blood sample, is transferred from outside apparatus 100 via receiving element 118 into sample composition chamber 104 and then on to treatment chamber 112 in a transferring step 214.

An antibody composition (Reagent A) 120 comprising CD64 antibodies is transferred via transfer element 107 to the treatment chamber 112 in a composition transfer step 204.

These two steps combined with mixing step 206 take around four minutes using cartridge 102 of the present invention.

A lysis buffer (Reagent B) 122 is also added and mixed with the resultant mixed composition. This step and mixing all the compositions takes around three minutes using cartridge 102 of the present invention. Reference beads (Reagent C) 308 are added to the treatment chamber.

The evaluation chamber 114 is configured and constructed for one or more evaluation steps 216.

According to some embodiments, the cartridge is introduced into a system as described in International patent application publication no. WO2011/128893 to Kasdan et al., incorporated herein by reference. This system has software associated therewith for computing the CD64 and CD163 indices on leukocytes.

The results of the evaluation step are then outputted in a results outputting step 218. According to this example, the time taken from the introduction of the small blood sample to obtaining an indication of sepsis is less than 15 minutes, typically around 10 minutes.

From a user point of view, the following steps are performed:

1) The user adds drop of blood to the cartridge 102 and seals it. (10 μL are metered out by microfluidics).
2) Blister A (106) is pressed, releasing 100 μL of Reagent A. Mixing in the cartridge is controlled by the cartridge handling unit (CHU), followed by a 4-minutes incubation.
3) Blister B (108) is pressed, releasing ~250 μL of Reagent B. Mixing in the cartridge is controlled by the CHU, followed by a 3-5-minutes incubation.
4) Magnetic stirbar is activated, stirring the bead suspension (Reagent C).
5) Blister C (110) is pressed, releasing 100 μL of Reagent C. Mixing in the cartridge is controlled by the CHU. According to one example, Reagent A is a mixture of murine monoclonal antibodies—diluted 1:5 in buffered saline (PBS+0.5% BSA); Reagent B is a Trillium Lyse solution (at working concentration); Reagent C is a suspension of 5.2 μm polystyrene beads labeled with Starfire Red and FITC, diluted 1:100 in PBS+0.01% Tween 20.
6) The sample is read by the optoelectronics core, and collected to the reading below.
7) Data is analyzed automatically and result is presented.
8) The cartridge is disposed as biohazard.

TABLE 2

Comparison of Prior art methodology with the methodology of the present invention for detecting sepsis using CD64 and CD163 antibodies.
LeukoDx device- present invention

| Step | Description | Volume (uL) | Duration (min) | comments |
|---|---|---|---|---|
| 1 | Mixing blood and antibodies | Blood- 10 Abs- 50 | 4 | |
| 2 | Adding RBC lysis buffer | 250 | 3 | Might require heating the buffer to 37 C. |
| 3 | Incubating, Vortexing | | 3 | |
| 4 | Adding normalization beads | 2 | Less than 1 | |
| 5 | Reading | | Less than 1 | |
| | Total | 312 | 10 | |

In the case of sepsis, by "normalization" is meant taking the ratio of the median of the target population fluorescence emission to the median of the reference bead population fluorescence emission.

According to some embodiments, the readout may comprise an optoelectronics core, which enables identification and detection of fluorescent signals.

The CCD in the core, used for focusing, can also be used to read chemiluminescent signals. The readout to user may also indicate where the result falls relative to reference ranges.

The contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

REFERENCES

Assicot, Marcel, et al. "High serum procalcitonin concentrations in patients with sepsis and infection." *The Lancet* 341.8844 (1993): 515-518.

Aulesa, C., et al. "Validation of the Coulter LH 750 in a hospital reference laboratory." *Laboratory Hematology* 9.1 (2003): 15-28.

Ault, Kenneth A. "Flow cytometric measurement of platelet function and reticulated platelets." *Annals of the New York Academy of Sciences* 677.1 (1993): 293-308.

Blajchman, Morris A., et al. "Bacterial detection of platelets: current problems and possible resolutions." *Transfusion medicine reviews* 19.4 (2005): 259-272.

Bodensteiner, David C. "A flow cytometric technique to accurately measure post-filtration white blood cell counts." *Transfusion* 29.7 (1989): 651-653.

Cheson, Bruce D., et al. "National Cancer Institute-sponsored Working Group guidelines for chronic lymphocytic leukemia: revised guidelines for diagnosis and treatment." *Blood* 87.12 (1996): 4990-4997.

Christ-Crain, Mirjam, et al. "Effect of procalcitonin-guided treatment on antibiotic use and outcome in lower respiratory tract infections: cluster-randomised, single-blinded intervention trial." *Lancet* 363.9409 (2004): 600-607.

Cristofanilli, Massimo, et al. "Circulating tumor cells, disease progression, and survival in metastatic breast cancer." *New England Journal of Medicine* 351.8 (2004): 781-791.

Davis, Bruce H., et al. "Neutrophil CD64 is an improved indicator of infection or sepsis in emergency department patients." *Archives of pathology & laboratory medicine* 130.5 (2006): 654-661.

Dieye, Tandakha Ndiaye, et al. "Absolute CD4 T-cell counting in resource-poor settings: direct volumetric measurements versus bead-based clinical flow cytometry instruments." *JAIDS Journal of Acquired Immune Deficiency Syndromes* 39.1 (2005): 32-37.

Divers, S. G., et al. "Quantitation of CD62, soluble CD62, and lysosome-associated membrane proteins 1 and 2 for evaluation of the quality of stored platelet concentrates." *Transfusion* 35.4 (2003): 292-297.

Drexler, Hans G., et al. "Diagnostic value of immunological leukemia phenotyping." *Acta haematologica* 76.1 (1986): 1-8.

Dziegiel, Morten Hanefeld, Leif Kofoed Nielsen, and Adela Berkowicz. "Detecting fetomaternal hemorrhage by flow cytometry." *Current opinion in hematology* 13.6 (2006): 490.

Fischer, Johannes C., et al. "Reducing costs in flow cytometric counting of residual white blood cells in blood products: utilization of a single platform bead free flow rate calibration method." *Transfusion* 51.7 (2011): 1431-1438.

Graff, Jochen, et al. "Close relationship between the platelet activation marker CD62 and the granular release of platelet-derived growth factor." *Journal of Pharmacology and Experimental Therapeutics* 300.3 (2002): 952-957.

Guerti, K., et al. "Performance evaluation of the PENTRA 60C+ automated hematology analyzer and comparison with the ADVIA 2120." *International journal of laboratory hematology* 31.2 (2009): 132-141.

Hawkins, Robert C. "Laboratory turnaround time." *The Clinical Biochemist Reviews* 28.4 (2007): 179.

Hershman, M. J., et al. "Monocyte HLA-DR antigen expression characterizes clinical outcome in the trauma patient." *British Journal of Surgery* 77.2 (2005): 204-207.

Hilfrich, Ralf, and Jalil Hariri. "Prognostic relevance of human papillomavirus L1 capsid protein detection within mild and moderate dysplastic lesions of the cervix uteri in combination with p16 biomarker." *Analytical and Quantitative Cytology and Histology* 30.2 (2008): 78-82.

Hillier, Sharon L., et al. "A case-control study of chorioamnionic infection and histologic chorioamnionitis in prematurity." New England Journal of Medicine 319.15 (1988): 972-978.

Hoffmann, Johannes JML. "Neutrophil CD64 as a sepsis biomarker." Biochemia Medica 21.3 (2011): 282-290.

Kibe, Savitri, Kate Adams, and Gavin Barlow. "Diagnostic and prognostic biomarkers of sepsis in critical care." Journal of Antimicrobial Chemotherapy 66.suppl 2 (2011): ii33-ii40.

LaRosa, Steven P., and Steven M. Opal. "Biomarkers: the future." Critical care clinics 27.2 (2011): 407.

Liu, N. I. N. G., A. H. Wu, and Shan S. Wong. "Improved quantitative Apt test for detecting fetal hemoglobin in bloody stools of newborns." Clinical chemistry 39.11 (1993): 2326-2329.

Lotan, Yair, et al. "Bladder cancer screening in a high risk asymptomatic population using a point of care urine based protein tumor marker." *The Journal of urology* 182.1 (2009): 52-58.

Masse, M., et al. "Validation of a simple method to count very low white cell concentrations in filtered red cells or platelets." *Transfusion* 32.6 (2003): 565-571.

Matic, Goran B., et al. "Whole blood analysis of reticulated platelets: improvements of detection and assay stability." *Cytometry* 34.5 (1998): 229-234.

McDonald, C. P., et al. "Use of a solid-phase fluorescent cytometric technique for the detection of bacteria in platelet concentrates." *Transfusion Medicine* 15.3 (2005): 175-183.

Michelson, Alan D. "Flow cytometry: a clinical test of platelet function." *Open Access Articles* (1996): 290.

Miller, E. M.; Freire, S. L. S.; Wheeler, A. R. "Proteomics in Microfluidic Devices" In *Encyclopedia of Micro- and Nanofluidics*; Li, D. Q., Ed.; Springer: Heidelberg, Germany, 2008; Vol. 3, pp 1749-1758."

Moro, Ricardo, et al. "A new broad-spectrum cancer marker." *Vitro Diagnostic Technology* (2005).

Perry, Sara E., et al. "Is low monocyte HLA-DR expression helpful to predict outcome in severe sepsis?." *Intensive care medicine* 29.8 (2003): 1245-1252.

Ramakumar, Sanjay, et al. "Comparison of screening methods in the detection of bladder cancer." *The Journal of urology* 161.2 (1999): 388-394.

Rawstron, Andy C., et al. "Quantitation of minimal disease levels in chronic lymphocytic leukemia using a sensitive flow cytometric assay improves the prediction of outcome and can be used to optimize therapy." *Blood* 98.1 (2001): 29-35.

Rodriguez, William R., et al. "A microchip CD4 counting method for HIV monitoring in resource-poor settings." *PLoS medicine* 2.7 (2005): e182.

Rylatt, D. B., et al. "An immunoassay for human D dimer using monoclonal antibodies." *Thrombosis research* 31.6 (1983): 767-778.

Sacks, David B., et al. "Guidelines and recommendations for laboratory analysis in the diagnosis and management of diabetes mellitus." *Clinical Chemistry* 48.3 (2002): 436-472.

Segal, H. C., et al. "Accuracy of platelet counting haematology analysers in severe thrombocytopenia and potential impact on platelet transfusion." *British Journal of Haematology* 128.4 (2005): 520-525.

Stein, Paul D., et al. "D-dimer for the exclusion of acute venous thrombosis and pulmonary embolism: a systematic review." *Annals of internal medicine* 140.8 (2004): 589.

Sutherland, D. Robert, et al. "The ISHAGE guidelines for CD34+ cell determination by flow cytometry." *Journal of hematotherapy* 5.3 (1996): 213-226.

Wang, Chao, et al. "Reticulated platelets predict platelet count recovery following chemotherapy." *Transfusion* 42.3 (2002): 368-374.

What is claimed is:

1. A method for assaying for possible infection or sepsis in a subject, comprising:
   a) applying a blood sample from the subject into a single-use microfluidic test cartridge, the test cartridge comprising:
      i) a sample composition chamber adapted for receiving the blood sample;

ii) a first pre-filled microfluidic blister comprising an antibody mixture comprising fluorescently tagged CD64 and fluorescently tagged CD 163 antibodies;

iii) a second pre-filled microfluidic blister comprising a cell lysis reagent;

iv) a third pre-filled microfluidic blister comprising fluorescently tagged beads having a fluorescent tag different than the fluorescent tag of the CD64 and the fluorescent tag of the CD163 antibodies;

v) a treatment compartment adapted for fluid mixing, wherein the treatment compartment is in fluid communication with the sample composition chamber, the first pre-filled microfluidic blister, the second pre-filled microfluidic blister, and the third pre-filled microfluidic blister;

vi) a bellow element fluidly connected to the treatment compartment;

vii) an evaluation chamber fluidly connected to the treatment compartment and comprising a reading zone;

b) inserting the test cartridge into a cartridge handling unit (CHU) wherein the CHU is pre-programmed to perform the following steps:

i) pressing the first pre-filled microfluidic blister thereby releasing the antibody mixture into the treatment compartment;

ii) mixing at least a portion of the blood sample and the antibody mixture in the treatment compartment for a predetermined period of time using the bellow element;

iii) pressing the second pre-filled microfluidic blister thereby releasing the cell lysis reagent into the treatment compartment;

iv) mixing the blood sample, the antibody mixture, and the cell lysis reagent in the treatment compartment for a predetermined period of time using the bellow element;

v) pressing the third pre-filled microfluidic blister thereby releasing the fluorescently tagged beads into the treatment compartment;

vi) mixing in the treatment compartment for a predetermined period of time, at least a portion of the blood sample, the antibody mixture, the cell lysis reagent, and the fluorescently tagged beads, thereby forming a final mixture;

vii) flowing individual blood cells and beads through the reading zone in the evaluation chamber;

viii) measuring fluorescent signals of fluorescently tagged blood cells using an optoelectronic unit;

ix) measuring fluorescent signals of the fluorescently tagged beads using the optoelectronic unit;

x) determining median fluorescence signal from the fluorescently tagged blood cells;

xi) determining median fluorescence signal from the fluorescently tagged beads;

xii) determining a ratio of the median fluorescence signals from steps (x) and (xi);

xiii) using the ratio to provide an index score representative of the possibility of infection or sepsis in the subject.

2. A method for assaying for possible infection or sepsis in a subject, comprising:

in a single-use microfluidic cartridge comprising a single-use blister, combining (i) a blood sample from the subject, (ii) an antibody mixture comprising fluorescently tagged CD64 and fluorescently tagged CD163 antibodies, (iii) fluorescently tagged beads having a fluorescent tag different than the antibody mixture, and (iv) a lysis reagent to thereby generate a final mixture;

in the single-use microfluidic cartridge, mixing the final mixture using a bellow element;

in the single-use microfluidic cartridge, flowing cells and beads from the final mixture into an evaluation chamber comprising a reading zone;

measuring fluorescent signals of fluorescently tagged blood cells using an optoelectronic unit;

measuring fluorescent signals of the fluorescently tagged beads using the optoelectronic unit;

determining median fluorescence signal from the fluorescently tagged blood cells;

determining median fluorescence signal from the fluorescently tagged beads;

determining a ratio of the median fluorescence signals from the fluorescently tagged blood cells and the fluorescently tagged beads; and using the ratio to provide an index score representative of the possibility of infection or sepsis in the subject.

3. The method of claim 1 or 2, wherein the test cartridge further comprises a pump or an air blowing element.

4. The method of claim 1 or 2, wherein the test cartridge is valveless.

5. The method of claim 1 or 2, wherein the volume of any of the microfluidic blisters is from about 1 microliter to 1000 microliters.

6. The method of claim 1 or 2, wherein the volume of the blood in the final mixture is about 10 microliters.

7. The method of claim 1, wherein the test cartridge based steps from the step of inserting the test cartridge into the CHU to the step of providing an index score are performed in less than 15 minutes.

8. The method of claim 2, wherein the steps from the step of combining the blood sample from the subject to the step of providing an index score are performed in less than 15 minutes.

9. The method of claim 1 or 2, wherein the cartridge further comprises a tortuous shaped channel.

10. The method of claim 1 or 2, wherein the fluorescently labeled beads comprise Starfire Red.

11. The method of claim 1, wherein the blood is whole blood.

12. The method of claim 1, wherein the cells comprise erythrocytes or leukocytes, and wherein the leukocytes comprise lymphocytes or neutrophils.

13. The method of claim 3, wherein the lysis reagent comprises ammonium chloride.

14. The method of claim 3, wherein, the antibodies are murine monoclonal antibodies.

15. The method of claim 1 or 2, wherein determining comprises employing at least one of crosscorrelation algorithm, boxar averaging algorithm, filtering algorithm or minimum mean square error fit.

16. The method of claim 1 or 2, further comprising determining the type of the cells.

* * * * *